United States Patent
Nishi et al.

(10) Patent No.: US 9,477,163 B2
(45) Date of Patent: Oct. 25, 2016

(54) ELECTROPHOTOGRAPHIC PHOTOSENSITIVE MEMBER, PROCESS CARTRIDGE, ELECTROPHOTOGRAPHIC APPARATUS, AND IMIDE COMPOUND

(71) Applicant: CANON KABUSHIKI KAISHA, Tokyo (JP)

(72) Inventors: Masashi Nishi, Susono (JP); Kunihiko Sekido, Suntou-gun (JP); Kei Tagami, Numazu (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/568,047

(22) Filed: Dec. 11, 2014

(65) Prior Publication Data

US 2015/0185637 A1 Jul. 2, 2015

(30) Foreign Application Priority Data

Dec. 26, 2013 (JP) .................................. 2013-269676
Apr. 7, 2014 (JP) .................................. 2014-079018
Dec. 5, 2014 (JP) .................................. 2014-246835

(51) Int. Cl.
*G03G 5/14* (2006.01)
*C07D 471/06* (2006.01)
*G03G 5/06* (2006.01)

(52) U.S. Cl.
CPC ............. *G03G 5/142* (2013.01); *C07D 471/06* (2013.01); *G03G 5/0651* (2013.01)

(58) Field of Classification Search
CPC ................................. G03G 5/14; G03G 5/142
See application file for complete search history.

(56) References Cited

U.S. PATENT DOCUMENTS 4,442,193 A 4/1984 Chen et al.
4,992,349 A 2/1991 Chen et al.
(Continued)

FOREIGN PATENT DOCUMENTS

EP 2 680 075 A1 1/2014
JP 2007-148294 A 6/2007
(Continued)

OTHER PUBLICATIONS

Hideo, "Coordination Control of Intramolecular electron transfer in Boronate-Bridged Zinc PorphyrinDiimide Molecules," The Journal of Organic Chemistry, vol. 65 No. 25, pp. 8747-8757.*

(Continued)

*Primary Examiner* — Peter Vajda
(74) *Attorney, Agent, or Firm* — Fitzpatrick, Cella, Harper & Scinto

(57) ABSTRACT

Provided is an electrophotographic photosensitive member including an undercoat layer that contains a polymerized product of a composition containing a compound represented by the formula (1).

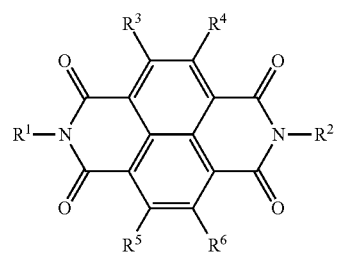

(1)

13 Claims, 5 Drawing Sheets

(56) References Cited

U.S. PATENT DOCUMENTS

| | | |
|---|---|---|
| 5,468,583 A | 11/1995 | Gruenbaum et al. |
| 8,546,050 B2 | 10/2013 | Maruyama et al. |
| 2006/0281020 A1 | 12/2006 | Kim et al. |

FOREIGN PATENT DOCUMENTS

| | | |
|---|---|---|
| JP | 2008-250082 A | 10/2008 |
| JP | 2014-215477 A | 11/2014 |

OTHER PUBLICATIONS

U.S. Appl. No. 14/564,969, filed Dec. 9, 2014. Inventor: Sekido, et al.

U.S. Appl. No. 14/568,043, filed Dec. 11, 2014. Inventor: Tagami, et al.

Yamashita, et al., "Crosslinking Agent Handbook", 1981, pp. 536-605.

Jones, et al., "Cyanonaphthalene Diimide Semiconductors for Air-Stable, Flexible, and Optically Transparent n-Channel Field-Effect Transistors", Chemistry of Materials, vol. 19, No. 11, May 29, 2007, pp. 2703-2705.

European Search Report dated Apr. 28, 2015 in European Application No. 14198755.2.

Shiratori, et al., "Coordination Control of Intramolecular Electron Transfer in Boronate-Bridged Zinc Porphyrin—Diimide Molecules", J. Org. Chem, vol. 65, 2000, pp. 8747-8757.

\* cited by examiner

ELECTROPHOTOGRAPHIC PHOTOSENSITIVE MEMBER, PROCESS CARTRIDGE, ELECTROPHOTOGRAPHIC APPARATUS, AND IMIDE COMPOUND

BACKGROUND OF THE INVENTION

1. Field of the Invention

The present invention relates to an electrophotographic photosensitive member, a process cartridge and an electrophotographic apparatus each including the electrophotographic photosensitive member, and an imide compound.

2. Description of the Related Art

An electrophotographic photosensitive member containing an organic photoconductive substance (charge-generating substance) has been mainly used as an electrophotographic photosensitive member to be mounted onto a process cartridge or an electrophotographic apparatus. The electrophotographic photosensitive member has the following advantage. The electrophotographic photosensitive member has good film formability and can be produced by application, and hence has high productivity.

The electrophotographic photosensitive member generally includes a support and a photosensitive layer formed on the support. In addition, an undercoat layer is often formed between the support and the photosensitive layer for the purpose of suppressing the injection of charge from the support toward the photosensitive layer to suppress the occurrence of an image defect such as a black spot. A charge-generating substance having additionally high sensitivity has been used in recent years. However, as the sensitivity of the charge-generating substance rises, the amount of charge to be generated increases. Accordingly, the charge is liable to remain in the photosensitive layer and hence a positive ghost is liable to occur. The positive ghost is a phenomenon in which during the formation of one image, the density of only a portion irradiated with light at the time of forward rotation increases.

Japanese Patent Application Laid-Open No. 2007-148294 and Japanese Patent Application Laid-Open No. 2008-250082 each describe a technology involving incorporating an electron-transporting substance into the undercoat layer as a technology for suppressing such positive ghost. In addition, Japanese Patent Application Laid-Open No. 2007-148294 and Japanese Patent Application Laid-Open No. 2008-250082 each describe the following technology. When the electron-transporting substance is incorporated into the undercoat layer, the undercoat layer is cured so that the electron-transporting substance may not be eluted in a solvent in an application liquid for the photosensitive layer at the time of the formation of the layer above the undercoat layer (photosensitive layer).

A requirement for the quality of an electrophotographic image does not cease to become more and more sophisticated nowadays, and hence tolerance for the positive ghost has become markedly strict.

In addition, studies made by the inventors of the present invention have found that the technology described in each of Japanese Patent Application Laid-Open No. 2007-148294 and Japanese Patent Application Laid-Open No. 2008-250082 is still susceptible to improvement in terms of a reduction in positive ghost.

SUMMARY OF THE INVENTION

An object of the present invention is to provide an electrophotographic photosensitive member suppressed in positive ghost, and a process cartridge and an electrophotographic apparatus each including the electrophotographic photosensitive member. Another object of the present invention is to provide an imide compound that can suppress a positive ghost.

According to one embodiment of the present invention, there is provided an electrophotographic photosensitive member, including:

a support;

an undercoat layer on the support; and a photosensitive layer on the undercoat layer, wherein the undercoat layer comprises a polymerized product of a composition including a compound represented by the following formula (1):

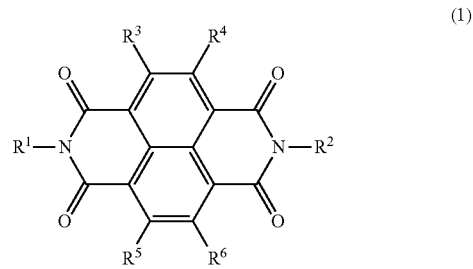

wherein, $R^1$ represents an alkyl group having 1 to 6 main-chain carbon atoms and having two or more polymerizable functional groups, a group derived from one of $CH_2$ in the main chain of the alkyl group having 1 to 6 main-chain carbon atoms substituted for an oxygen atom and having two or more polymerizable functional groups, a group derived from one of $CH_2$ in the main chain of the alkyl group having 1 to 6 main-chain carbon atoms substituted for a sulfur atom and having two or more polymerizable functional groups, or a group derived from one of $CH_2$ in the main chain of the alkyl group having 1 to 6 main-chain atoms substituted for $NR^7$ and having two or more polymerizable functional groups, the polymerizable functional groups is a hydroxy group, a thiol group, an amino group, or a carboxyl group;

$R^7$ represents a hydrogen atom or an alkyl group;

$R^2$ represents an unsubstituted or substituted alkyl group having 1 to 6 main-chain carbon atoms, a group having 1 to 6 main chain atoms and derived from one of $CH_2$ in a main chain of an un substituted or substituted alkyl group substituted for an oxygen atom, a group having 1 to 6 main chain atoms and derived from one of $CH_2$ in the main chain of an unsubstituted or substituted alkyl group substituted for a sulfur atom, a group having 1 to 6 main chain atoms and derived from one of $CH_2$ in the main chain of an unsubstituted or substituted alkyl group substituted for $NR^8$, or a substituted aryl group, and $R^8$ represents a hydrogen atom or an alkyl group;

a substituent of the substituted alkyl group is an alkyl group having 1 to 6 carbon atoms, a benzyl group, an alkoxycarbonyl group, or a phenyl group;

a substituent of the substituted aryl group is a halogen atom, a cyano group, a nitro group, a methyl group, an ethyl group, an isopropyl group, a n-propyl group, a n-butyl group, an acyl group, an alkoxycarbonyl group, an alkoxy group, a thioalkoxy group, or an aminoalkoxy group, and an atomic number of all substituent except for hydrogen atoms, which the aryl group has, is 4 or more; and $R^3$ to $R^6$ each independently represent a hydrogen atom, a halogen atom, a cyano group, a nitro group, an unsubstituted or substituted alkyl group, or an unsubstituted or substituted aryl group.

The present invention also relates to a process cartridge, including: the electrophotographic photosensitive member; and at least one unit selected from the group consisting of a charging unit, a developing unit, and a cleaning unit, the process cartridge integrally supporting the electrophotographic photosensitive member and the at least one unit, the process cartridge being removably mounted onto a main body of an electrophotographic apparatus.

The present invention also relates to an electrophotographic apparatus, including: the electrophotographic photosensitive member; a charging unit; an exposing unit; a developing unit; and a transferring unit.

The present invention also relates to an imide compound represented by the formula (1).

According to embodiments of the present invention, it is possible to provide the electrophotographic photosensitive member suppressed in positive ghost, and the process cartridge and the electrophotographic apparatus each including the electrophotographic photosensitive member. According to another embodiment of the present invention, it is possible to provide the imide compound that can suppress a positive ghost.

Further features of the present invention will become apparent from the following description of exemplary embodiments with reference to the attached drawings.

DESCRIPTION OF THE EMBODIMENTS

Figure 1:
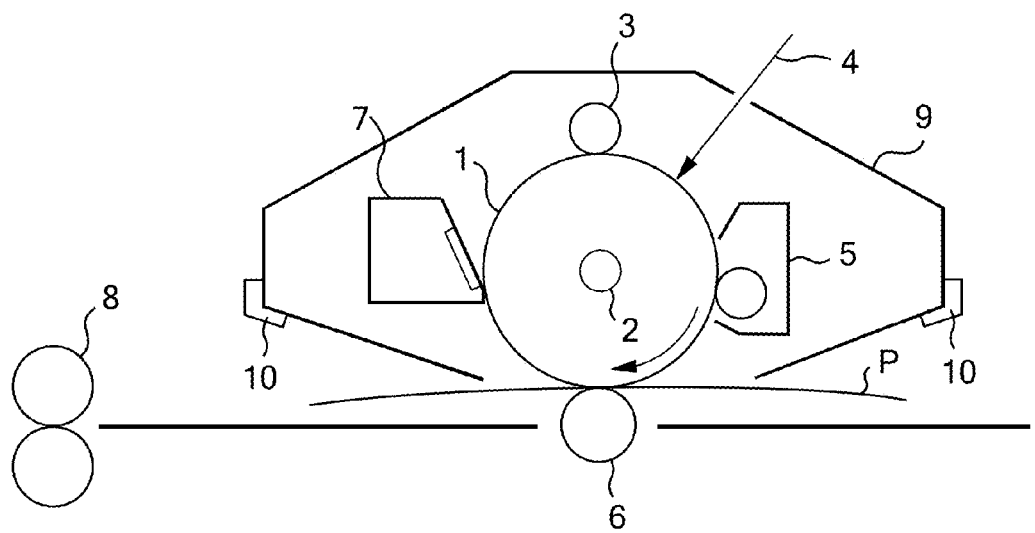
FIG. 1 is a view illustrating the schematic construction of an electrophotographic apparatus including a process cartridge including an electrophotographic photosensitive member.

The present invention has a feature in that the undercoat layer of an electrophotographic photosensitive member contains a polymerized product of a composition containing a compound represented by the following formula (1):

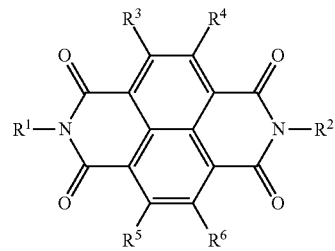

wherein, $R^1$ represents an alkyl group having 1 to 6 main-chain carbon atoms and having two or more polymerizable functional groups, a group derived from one of $CH_2$ in the main chain of the alkyl group having 1 to 6 main-chain carbon atoms substituted for an oxygen atom and having two or more polymerizable functional groups, a group derived from one of $CH_2$ in the main chain of the alkyl group having 1 to 6 main-chain carbon atoms substituted for a sulfur atom and having two or more polymerizable functional groups, or a group derived from one of $CH_2$ in the main chain of the alkyl group having 1 to 6 main-chain atoms substituted for $NR^7$ and having two or more polymerizable functional groups, the polymerizable functional groups is a hydroxy group, a thiol group, an amino group, or a carboxyl group;

$R^7$ represents a hydrogen atom or an alkyl group;

$R^2$ represents an unsubstituted or substituted alkyl group having 1 to 6 main-chain carbon atoms, a group having 1 to 6 main chain atoms and derived from one of $CH_2$ in a main chain of an un substituted or substituted alkyl group substituted for an oxygen atom, a group having 1 to 6 main chain atoms and derived from one of $CH_2$ in the main chain of an unsubstituted or substituted alkyl group substituted for a sulfur atom, a group having 1 to 6 main chain atoms and derived from one of $CH_2$ in the main chain of an unsubstituted or substituted alkyl group substituted for $NR^B$, or a substituted aryl group, and $R^8$ represents a hydrogen atom or an alkyl group;

a substituent of the substituted alkyl group is an alkyl group having 1 to 6 carbon atoms, a benzyl group, an alkoxycarbonyl group, or a phenyl group;

a substituent of the substituted aryl group is a halogen atom, a cyano group, a nitro group, a methyl group, an ethyl group, an isopropyl group, a n-propyl group, a n-butyl group, an acyl group, an alkoxycarbonyl group, an alkoxy group, a thioalkoxy group, or an aminoalkoxy group, and an atomic number of all substituent except for hydrogen atoms, which the aryl group has, is 4 or more; and $R^3$ to $R^6$ each independently represent a hydrogen atom, a halogen atom, a cyano group, a nitro group, an unsubstituted or substituted alkyl group, or an unsubstituted or substituted aryl group.

The inventors of the present invention have assumed the reason why a positive ghost is reduced when the undercoat layer contains the polymerized product to be as described below.

One possible factor for the occurrence of the positive ghost is an electron trap due to an increase in distance between molecules of an electron-transporting substance. When the electron trap is formed in the undercoat layer, the electron-transporting property of the undercoat layer is liable to reduce and hence residual charge is liable to generate. Probably as a result of the foregoing, the residual charge is liable to accumulate at the time of long-term repeated use of the electrophotographic photosensitive member and hence the positive ghost occurs.

In the present invention, two or more hydrogen-bonding polymerizable functional groups such as a hydroxy group and a carboxyl group are present on one side of the compound (electron-transporting substance) represented by the formula (1), and the opposite side thereof is free of such hydrogen-bonding polymerizable functional groups and has a relatively bulky structure. The inventors have considered that in this case, the molecules of the electron-transporting substance can exist so as to be relatively close to each other by virtue of an interaction between the hydrogen-bonding polymerizable functional groups on one side. Further, the inventors have considered that the electron trap due to the agglomeration of the molecules of the electron-transporting substance can also be suppressed by the bulky structure. The inventors have assumed that the positive ghost is reduced as a result of the foregoing.

The bulky structure is a structure corresponding to $R^2$ of the compound represented by the formula (1).

$R^2$ has a carbon chain having 1 to 6 main-chain carbon atoms. The inventors have considered that because of a high degree of freedom of the carbon chain having 1 to 6 main-chain carbon atoms, even when the number of carbon atoms of its main chain is relatively small, the agglomeration and the like of the molecules of the electron-transporting substance can be suppressed.

When $R^2$ represents a substituted aryl group, the total number of atoms except hydrogen atoms of all the substituents of the aryl group is 4 or more. Examples of the atoms except hydrogen atoms include a carbon atom, an oxygen atom, a nitrogen atom, a sulfur atom, and a halogen atom. The total number of the atoms except hydrogen atoms of all the substituents of the aryl group is as described below. For example, when the aryl group has one methyl group and one ethyl group as substituents, the number of the atoms except hydrogen atoms is 3. In addition, when the aryl group has two isopropyl groups as substituents, the number of the atoms except hydrogen atoms is 6. The compound represented by the formula (1) has a structure having sterically strong planarity. The inventors have considered that because of the structure, stacking between its molecules is strong, and hence when the number of the atoms except hydrogen atoms is 3 or less, the agglomeration of the molecules of the electron-transporting substance cannot be suppressed. In addition, the inventors have considered that when a bulky substituent, for example, a substituent like a t-Bu group or a phenyl group is bonded as a substituent of the aryl group, the electron-transporting property is liable to reduce owing to its steric hindrance.

It is assumed that when a plurality of hydrogen-bonding polymerizable functional groups (substituents) are present on both sides of the electron-transporting substance, the interaction strongly acts and hence the molecules of the electron-transporting substance are liable to agglomerate.

The content of a polymerized product of the compound represented by the formula (1) or the polymerized product of the composition containing the compound represented by the formula (1) in the undercoat layer is preferably 50 mass % or more and 100 mass % or less with respect to the total mass of the undercoat layer. Further, the content is more preferably 80 mass % or more and 100 mass % or less.

[Electron-Transporting Substance]

The undercoat layer of the present invention contains the polymerized product of the composition containing the compound represented by the formula (1).

When the undercoat layer contains the polymerized product of the composition containing the compound represented by the formula (1), the composition preferably further contains a crosslinking agent, or the crosslinking agent and a resin.

In the compound represented by the formula (1), $R^1$ preferably represents an alkyl group having 1 to 3 main-chain carbon atoms and having 2 or more polymerizable functional groups, a group derived from one of the $CH_2$ in a main chain of the alkyl group having 1 to 3 main-chain carbon atoms substituted for an oxygen atom and having 2 or more polymerizable functional groups, a group derived from one of $CH_2$ in the main chain of the alkyl group having 1 to 3 main-chain carbon atoms substituted for a sulfur atom and having 2 or more polymerizable functional groups, or a group derived from one of $CH_2$ in the main chain of the alkyl group having 1 to 3 main-chain carbon atoms substituted for $NR^7$ and having 2 or more polymerizable functional groups.

Further, $R^2$ preferably represents a monovalent group represented by the following formula (2) or a monovalent group represented by the following formula (3). The presence of any such monovalent group may suppress the electron trap and hence make the electrophotographic photosensitive member additionally excellent in degree of suppression of the positive ghost.

(2)

In the formula (2), $L^1$ represents a hydrogen atom;

$L^2$ and $L^3$ each independently represent represents an unsubstituted or substituted alkyl group having 1 to 6 main-chain carbon atoms, a group having 1 to 6 main chain atoms and derived from one of $CH_2$ in a main chain of an unsubstituted or substituted alkyl group substituted for an oxygen atom, a group having 1 to 6 main chain atoms and derived from one of $CH_2$ in the main chain of an unsubstituted or substituted alkyl group substituted for a sulfur atom, a group having 1 to 6 main chain atoms and derived from one of $CH_2$ in the main chain of an unsubstituted or substituted alkyl group substituted for $NR^8$, or a substituted or unsubstituted aryl group; and a substituent of the substituted alkyl group is an alkyl group having 1 to 6 carbon atoms, a benzyl group, an alkoxycarbonyl group, or a phenyl group.

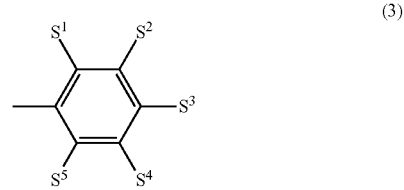

(3)

In the formula, $S^1$ represents a methyl group, an ethyl group, an isopropyl group, a n-propyl group, a n-butyl group, an acyl group, an alkoxycarbonyl group, a methoxy group, an ethoxy group, a thiomethoxy group, a thioethoxy group, an aminomethoxy group, or an aminoethoxy group.

$S^2$ to $S^5$ each independently represent a hydrogen atom, a halogen atom, a cyano group, a nitro group, a methyl group, an ethyl group, an isopropyl group, a n-propyl group, a n-butyl group, an acyl group, an alkoxycarbonyl group, an alkoxy group, a thioalkoxy group, or an aminoalkoxy group.

In addition, in the present invention, the compound represented by the formula (1) is given as an example of an imide compound that can suppress the positive ghost.

[Crosslinking Agent]

A compound that polymerizes (cures) or crosslinks with the compound (electron-transporting substance) represented by the formula (1) can be used as the crosslinking agent. Specifically, for example, a compound described in the "Crosslinking Agent Handbook" edited by Shinzo Yamashita and Tosuke Kaneko, and published by TAISEI-SHA LTD. (1981) can be used.

Examples of the crosslinking agent include the following isocyanate compounds having an isocyanate group or a blocked isocyanate group and amine compounds having an N-methylol group or an alkyl-etherified N-methylol group. However, the present invention is not limited thereto. In addition, a plurality of crosslinking agents may be used in combination.

The isocyanate compound is preferably an isocyanate compound having a plurality of (two or more) isocyanate groups or blocked isocyanate groups. Examples thereof include triisocyanatobenzene, triisocyanatomethylbenzene, triphenylmethane triisocyanate, lysine triisocyanate, and an isocyanurate modified product, biuret modified product, allophanate modified product, and trimethylolpropane or pentaerythritol adduct modified product of a diisocyanate such as tolylene diisocyanate, hexamethylene diisocyanate, dicyclohexylmethane diisocyanate, naphthalenediisocyanato, diphenylmethane diisocyanate, isophorone diisocyanate, xylylene diisocyanate, 2,2,4-trimethylhexamethylene diisocyanate, methyl-2,6-diisocyanatohexanoate, or norbornane diisocyanate. Of those, an isocyanurate modified product and an adduct modified product are more preferred.

As an isocyanate compound (crosslinking agent) that may be purchased, there are given, for example: an isocyanate-based crosslinking agent such as DURANATE MFK-60B or SBA-70B manufactured by Asahi Kasei Corporation or Desmodur BL3175, BL3475 or BL3575 manufactured by Sumika Bayer Urethane Co., Ltd.; an amino-based crosslinking agent such as U-VAN 20SE60 or 220 manufactured by Mitsui Chemicals, Inc., or SUPER BECKAMINE L-125-60 or G-821-60 manufactured by DIC Corporation; and an acrylic crosslinking agent such as FANCRYL FA-129AS or FA-731A manufactured by Hitachi Chemical Co., Ltd.

For example, the amine compound is preferably an amine compound having a plurality of (two or more) N-methylol groups or alkyl-etherified N-methylol groups. Examples thereof include methylolated melamine, methylolated guanamine, a methylolated urea derivative, a methylolated ethylene urea derivative, methylolated glycoluril, compounds obtained by alkyl-etherifying the methylol moieties of the foregoing compounds, and derivatives thereof.

As an amine compound (crosslinking agent) that may be purchased, there are given, for example, SUPER MELAMI No. 90 (manufactured by NOF CORPORATION), SUPER BECKAMINE™ TD-139-60, L-105-60, L127-60, L110-60, J-820-60, J821-60, G-821-60 or P138 (manufactured by DIC Corporation), U-VAN 2020 (Mitsui Chemicals, Inc.), Sumitex Resin M-3 (Sumitomo Chemical Company), NIKALAC MW-30, MW-390, or MX-750LM (manufactured by NIPPON CARBIDE INDUSTRIES CO., INC.), "SUPER BECKAMINE™ L-148-55, 13-535, L-145-60, or TD-126 (manufactured by DIC Corporation), NIKALAC BL-60 or BX-4000 (manufactured by NIPPON CARBIDE INDUSTRIES CO., INC.), and NIKALAC MX-280, NIKALAC MX-270, or NIKALAC MX-290 (manufactured by NIPPON CARBIDE INDUSTRIES CO., INC.).

[Resin]

A resin having a polymerizable functional group that can polymerize (cure) with the compound represented by the formula (1) can be used as the resin. Preferred examples of the polymerizable functional group include a hydroxy group, a thiol group, an amino group, a carboxyl group, and a methoxy group.

Examples of the resin having the polymerizable functional group include a polyether polyol resin, a polyester polyol resin, an acrylic polyol resin, a polyvinyl alcohol resin, a polyvinyl acetal resin, a polyamide resin, a carboxyl group-containing resin, a polyamine resin, and a polythiol resin. The present invention is not limited thereto. In addition, a plurality of resins may be used in combination.

Examples of the resin having the polymerizable functional group that may be purchased include: a polyether polyol-based resin such as AQD-457 or AQD-473 manufactured by Nippon Polyurethane Industry Co., Ltd., or SANNIX GP-400 or GP-700 manufactured by Sanyo Chemical Industries, Ltd.; a polyester polyol-based resin such as PHTHALKYD W2343 manufactured by Hitachi Chemical Co., Ltd., WATERSOL S-118 or CD-520 manufactured by DIC Corporation, or HARIDIP WH-1188 manufactured by Harima Chemicals; an acrylic polyol-based resin such as BURNOCK WE-300 or WE-304 manufactured by DIC Corporation; a polyvinyl alcohol-based resin such as KURARAY POVAL PVA-203 manufactured by KURARAY CO., LTD.; a polyvinyl acetal-based resin such as BX-1, BM-1, KS-1, or KS-5 manufactured by SEKISUI CHEMICAL CO., LTD.; a polyamide-based resin such as TORESIN FS-350 manufactured by Nagase ChemteX Corporation; a carboxyl group-containing resin such as AQUALIC manufactured by NIPPON SHOKUBAI CO., LTD. or FINELEX SG2000 manufactured by Namariichi Co., Ltd.; a polyamine resin such as LUCKAMIDE manufactured by DIC Corporation; and a polythiol resin such as QE-340M manufactured by Toray Fine Chemicals Co., Ltd.

The weight-average molecular weight of the resin having the polymerizable functional group more preferably falls within the range of from 5,000 to 400,000. The weight-average molecular weight of the resin having the polymerizable functional group is more preferably from 5,000 to 300,000.

A mass ratio between the compound represented by the formula (1), and the crosslinking agent and/or the resin having the polymerizable functional group in the composition is preferably from 100:50 to 100:250 from the viewpoint of suppressing the positive ghost.

The undercoat layer may contain any other resin (resin free of any polymerizable functional group), an organic particle, an inorganic particle, a leveling agent, or the like in addition to the polymerized product in order that the film formability and electrical characteristics of the electrophotographic photosensitive member may be improved. It should be noted that the content of any such material in the undercoat layer is preferably 50 mass % or less, more preferably 20 mass % or less with respect to the total mass of the undercoat layer.

The undercoat layer can be formed by: forming a coating film of an application liquid for the undercoat layer containing the composition containing the compound represented by the formula (1); and drying the coating film. At the time of the drying of the coating film of the application liquid for the undercoat layer, the compound represented by the formula (1) polymerizes. The polymerization reaction (curing reaction) is accelerated by applying heat energy or light energy at that time.

A solvent to be used in the application liquid for the undercoat layer is, for example, an alcohol-based solvent, a sulfoxide-based solvent, a ketone-based solvent, an ether-based solvent, an ester-based solvent, or an aromatic hydrocarbon solvent.

Specific examples of the electron-transporting substance are shown below. However, the present invention is not limited thereto. In addition, a plurality of electron-transporting substances may be used in combination.

TABLE 1

| Exemplified Compound | R3 | R4 | R5 | R6 | R1 | R2 L1 | L2 | L3 |
|---|---|---|---|---|---|---|---|---|
| 101 | H | H | H | H | HO—CH$_2$—CH(—)—CH$_2$—OH | H | n-C$_3$H$_7$ | n-C$_3$H$_7$ |
| 102 | H | H | H | H | HO—CH$_2$—CH(—)—CH$_2$—OH | H | CH$_3$ | n-C$_5$H$_{11}$ |
| 103 | H | H | H | H | HO—CH$_2$—CH(—)—CH$_2$—OH | H | C$_2$H$_5$ | CH$_2$OCH$_3$ |
| 104 | H | H | H | H | HO—CH$_2$—CH(—)—CH$_2$—OH | H | COOC$_2$H$_5$ | CH$_2$CH(CH$_3$)$_2$ |
| 105 | H | H | H | H | HO—CH$_2$—CH(—)—CH$_2$—OH | H | COOCH$_3$ | C$_2$H$_4$SCH$_3$ |
| 106 | H | H | H | H | HO—CH$_2$—CH(—)—CH$_2$—OH | H | COOC$_2$H$_5$ | COOC$_2$H$_5$ |
| 107 | H | H | H | H | HO—CH$_2$—CH(—)—CH$_2$—OH | H | COOCH$_3$ | CH$_2$Ph |
| 108 | H | H | H | H | HO—CH$_2$—CH(—)—CH$_2$—OH | H | CH$_3$ | COOC(CH$_3$)$_3$ |
| 109 | H | H | H | H | HO—CH$_2$—CH(—)—CH$_2$—OH | H | COOCH$_3$ | CH$_2$NHCH$_3$ |
| 110 | H | H | H | H | HO—CH$_2$—CH(—)—CH$_2$—OH | H | CH$_3$ | C$_3$H$_6$N(C$_2$H$_5$)$_2$ |
| 111 | H | H | H | H | HO—CH$_2$—CH(—)—CH$_2$—OH | H | CH$_3$ | C$_2$H$_4$Ph |

TABLE 1-continued

| Exemplified Compound | R3 | R4 | R5 | R6 | R1 | R2 L1 | R2 L2 | R2 L3 |
|---|---|---|---|---|---|---|---|---|
| 112 | H | H | H | H | HO—CH₂\CH—/HO—CH₂ | CH₃ | CH₃ | C₂H₅ |
| 113 | H | H | H | H | HO—CH₂\CH—/HO—CH₂ | CH₃ | CH₃ | COOC(CH₃)₃ |
| 114 | H | H | H | H | HO—CH₂\CH—/HO—CH₂ | H | H | n-C₆H₁₃ |
| 115 | H | H | H | H | HO—CH₂\CH—/HO—CH₂ | H | H | C₂H₄SC₂H₅ |
| 116 | H | H | H | H | HO—CH₂\CH—/HO—CH₂ | H | H | CH₂CH(OC₂H₅)₂ |
| 117 | H | H | H | H | HO—CH₂\CH—/HO—CH₂ | H | H | C₂H₄N(CH₃)₂ |
| 118 | H | H | H | H | HO\CH—CH₂—/HO—CH₂ | H | n-C₃H₇ | n-C₃H₇ |
| 119 | H | H | H | H | HO\CH—CH₂—/HO—CH₂ | H | COOC₂H₅ | CH₂CH(CH₃)₂ |
| 120 | H | H | H | H | HO\CH—CH₂—/HO—CH₂ | H | CH₃ | C₃H₆N(C₂H₅)₂ |
| 121 | H | H | H | H | HO\CH—CH₂—/HO—CH₂ | H | H | C₂H₄SC₂H₅ |
| 122 | H | H | H | H | HO\CH—CH₂—/HO—CH₂ | H | H | CH₂CH(OC₂H₅)₂ |
| 123 | H | H | H | H | HO—C₂H₄\N—C₃H₆—/HO—C₂H₄ | H | n-C₃H₇ | n-C₃H₇ |

TABLE 2

| Exemplified Compound | R3 | R4 | R5 | R6 | R1 | R2 L1 | R2 L2 | R2 L3 |
|---|---|---|---|---|---|---|---|---|
| 124 | H | H | H | H | HO—C₂H₄\\N—C₃H₆—/HO—C₂H₄ | H | COOC₂H₅ | CH₂CH(CH₃)₂ |
| 125 | H | H | H | H | HO—CH₂, H₃C—C, HO—CH₂ | H | n-C₃H₇ | n-C₃H₇ |
| 126 | H | H | H | H | HO—CH₂\\CH—/HO—CH\\Ph | H | CH₃ | n-C₅H₁₁ |
| 127 | CN | H | H | CN | HO—CH₂\\CH—/HO—CH₂ | H | n-C₃H₇ | n-C₃H₇ |
| 128 | H | NO₂ | NO₂ | H | HO—CH₂\\CH—/HO—CH₂ | H | n-C₃H₇ | n-C₃H₇ |
| 129 | Br | H | H | Br | HO—CH₂\\CH—/HO—CH₂ | H | n-C₃H₇ | n-C₃H₇ |
| 130 | CH₃ | H | H | CH₃ | HO—CH₂\\CH—/HO—CH₂ | H | n-C₃H₇ | n-C₃H₇ |
| 131 | H | Cl | Cl | H | HO—CH₂\\CH—/HO—CH₂ | H | n-C₃H₇ | n-C₃H₇ |

TABLE 3

| Exemplified Compound | R3 | R4 | R5 | R6 | R1 | R2 L1 | R2 L2 | R2 L3 |
|---|---|---|---|---|---|---|---|---|
| 132 | H | H | H | H | HOOC\\CH—/HO—CH₂ | H | CH₃ | n-C₅H₁₁ |
| 133 | H | H | H | H | HOOC\\CH—/HO—CH₂ | H | C₂H₅ | CH₂OCH₃ |
| 134 | H | H | H | H | HOOC\\CH—/HS—CH₂ | H | n-C₃H₇ | n-C₃H₇ |

TABLE 3-continued

| Exemplified Compound | R3 | R4 | R5 | R6 | R1 | R2 L1 | R2 L2 | R2 L3 |
|---|---|---|---|---|---|---|---|---|
| 135 | H | H | H | H | HOOC-CH(-CH$_2$-SH)- | H | COOCH$_3$ | C$_2$H$_4$SCH$_3$ |
| 136 | H | H | H | H | HO-CH(-CH$_2$-NH$_2$)-CH$_2$- | H | CH$_3$ | n-C$_5$H$_{11}$ |
| 137 | H | H | H | H | HO-CH(-CH$_2$-NH$_2$)-CH$_2$- | H | C$_2$H$_5$ | CH$_2$OCH$_3$ |
| 138 | H | H | H | H | HOOC-CH(-C$_2$H$_4$-OH)- | H | CH$_3$ | n-C$_5$H$_{11}$ |
| 139 | H | H | H | H | HOOC-CH(-C$_2$H$_4$-SH)- | H | n-C$_3$H$_7$ | n-C$_3$H$_7$ |
| 140 | H | H | H | H | HOOC-CH(OH)-C$_2$H$_4$- | H | CH$_3$ | n-C$_5$H$_{11}$ |

TABLE 4

| Exemplified Compound | R3 | R4 | R5 | R6 | R1 | R2 L1 | R2 L2 | R2 L3 |
|---|---|---|---|---|---|---|---|---|
| 141 | H | H | H | H | C(CH$_2$OH)$_3$- | H | CH$_3$ | n-C$_5$H$_{11}$ |
| 142 | H | H | H | H | HOOC-CH(-CH(OH)-COOH)- | H | n-C$_3$H$_7$ | n-C$_3$H$_7$ |
| 143 | H | H | H | H | OHC-CH(-CH(OH)-CH(OH)-C$_2$H$_4$-OH)- | H | CH$_3$ | n-C$_5$H$_{11}$ |
| 144 | H | H | H | H | HOCH$_2$-CH(OH)-CH(OH)-CH(OH)-CH(OH)-CH$_2$- | H | n-C$_3$H$_7$ | n-C$_3$H$_7$ |

TABLE 5

| Exemplified Compound | R3 | R4 | R5 | R6 | R1 | R2 | | |
|---|---|---|---|---|---|---|---|---|
| | | | | | | L1 | L2 | L3 |
| 145 | H | H | H | H | HO—CH$_2$\\CH—/HO—CH$_2$ | H | COOCH$_3$ | CH$_2$CH(CH$_3$)$_2$ |
| 146 | H | H | H | H | HO—CH$_2$\\CH—/HO—CH$_2$ | H | COOCH$_3$ | CH(CH$_3$)C$_2$H$_5$ |
| 147 | H | H | H | H | HO—CH$_2$\\CH—/HO—CH$_2$ | H | COOC$_2$H$_5$ | C$_3$H$_7$ |
| 148 | H | H | H | H | HO—CH$_2$\\CH—/HO—CH$_2$ | H | COOCH$_3$ | C$_2$H$_4$COOCH$_3$ |
| 149 | H | H | H | H | HO—CH$_2$\\CH—/HO—CH$_2$ | H | COOC$_2$H$_5$ | C$_2$H$_4$COOC$_2$H$_5$ |
| 150 | H | H | H | H | HO—CH$_2$\\CH—/HO—CH$_2$ | H | COOC(CH$_3$)$_3$ | CH(CH$_3$)OC(CH$_3$)$_3$ |
| 151 | H | H | H | H | HO—CH$_2$\\CH—/HO—CH$_2$ | H | CH$_3$ | Ph |
| 152 | H | H | H | H | HO—CH$_2$\\CH—/HO—CH$_2$ | H | CH$_3$ |  |
| 153 | H | H | H | H | HO—CH$_2$\\CH—/HO—CH$_2$ | H | CH$_3$ | 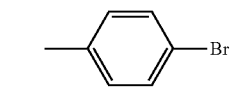 |
| 154 | H | H | H | H | HO—CH$_2$\\CH—/HO—CH$_2$ | H | CH$_3$ |  |
| 155 | H | H | H | H | HO—CH$_2$\\CH—/HO—CH$_2$ | H | CH$_3$ | 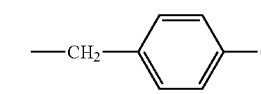 |
| 156 | H | H | H | H | HO—CH$_2$\\CH—/HO—CH$_2$ | H | Ph | Ph |
| 157 | H | H | H | H | HO—CH$_2$\\CH—/HO—CH$_2$ | H | CH$_3$ | 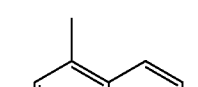 |

TABLE 5-continued

| Exemplified Compound | R3 | R4 | R5 | R6 | R1 | R2 L1 | R2 L2 | R2 L3 |
|---|---|---|---|---|---|---|---|---|
| 158 | H | H | H | H | HO\CH−CH$_2$−/HO−CH$_2$ | H | CH$_3$ | n-C$_5$H$_{11}$ |
| 159 | H | H | H | H | HO\CH−CH$_2$−/HO−CH$_2$ | H | COOC$_2$H$_5$ | COOC$_2$H$_5$ |
| 160 | H | H | H | H | HO\CH−CH$_2$−/HO−CH$_2$ | H | COOC$_2$H$_5$ | C$_2$H$_4$COOC$_2$H$_5$ |
| 161 | H | H | H | H | HO\CH−CH$_2$−/HO−CH$_2$ | H | CH$_3$ | Ph |
| 162 | H | H | H | H | HO\CH−CH$_2$−/HO−CH$_2$ | H | Ph | Ph |

Tables 1 to 5 show cases where R$^2$ in the compound represented by the formula (1) represents a monovalent group represented by the formula (2).

TABLE 6

| Exemplified Compound | R3 | R4 | R5 | R6 | R1 | R2 S1 | S2 | S3 | S4 | S5 |
|---|---|---|---|---|---|---|---|---|---|---|
| 201 | H | H | H | H | HO−CH$_2$\CH−/HO−CH$_2$ | C$_2$H$_5$ | H | H | H | C$_2$H$_5$ |
| 202 | H | H | H | H | HO−CH$_2$\CH−/HO−CH$_2$ | CH(CH$_3$)$_2$ | H | H | H | CH(CH$_3$)$_2$ |
| 203 | H | H | H | H | HO−CH$_2$\CH−/HO−CH$_2$ | COOC$_2$H$_5$ | H | H | H | H |
| 204 | H | H | H | H | HO−CH$_2$\CH−/HO−CH$_2$ | OCH$_3$ | H | H | OCH$_3$ | H |
| 205 | H | H | H | H | HO−CH$_2$\CH−/HO−CH$_2$ | CH$_3$ | H | n-C$_4$H$_9$ | H | H |
| 206 | H | H | H | H | HO−CH$_2$\CH−/HO−CH$_2$ | C$_2$H$_5$ | H | CN | H | H |

TABLE 6-continued

| Exemplified Compound | R3 | R4 | R5 | R6 | R1 | R2 | | | | |
|---|---|---|---|---|---|---|---|---|---|---|
| | | | | | | S1 | S2 | S3 | S4 | S5 |
| 207 | H | H | H | H | HO—CH$_2$\\CH—/HO—CH$_2$ | n-C$_3$H$_7$ | H | CH$_3$ | H | H |
| 208 | H | H | H | H | HO—CH$_2$\\CH—/HO—CH$_2$ | n-C$_4$H$_9$ | H | H | H | H |
| 209 | H | H | H | H | HO—CH$_2$\\CH—/HO—CH$_2$ | OC$_2$H$_5$ | H | CH$_3$ | H | H |
| 210 | H | H | H | H | HO—CH$_2$\\CH—/HO—CH$_2$ | SCH$_3$ | H | CF$_3$ | H | H |
| 211 | H | H | H | H | HO—CH$_2$\\CH—/HO—CH$_2$ | SC$_2$H$_5$ | H | H | CF$_3$ | H |
| 212 | H | H | H | H | HO—CH$_2$\\CH—/HO—CH$_2$ | NHCH$_3$ | H | CF$_3$ | H | H |
| 213 | H | H | H | H | HO—CH$_2$\\CH—/HO—CH$_2$ | NHC$_2$H$_5$ | H | H | Cl | H |
| 214 | H | H | H | H | HO—CH$_2$\\CH—/HO—CH$_2$ | OCH$_3$ | H | H | OPh | H |
| 215 | H | H | H | H | HO—CH$_2$\\CH—/HO—CH$_2$ | COOCH$_3$ | H | H | COOCH$_3$ | H |
| 216 | H | H | H | H | HO—CH$_2$\\CH—/HO—CH$_2$ | H | CH$_3$ | CH(CH$_3$)$_2$ | H | H |
| 217 | H | H | H | H | HO—CH$_2$\\CH—/HO—CH$_2$ | H | H | CH$_2$Ph | H | H |
| 218 | H | H | H | H | HO—CH$_2$\\CH—/HO—CH$_2$ | H | H | CO(n-C$_3$H$_7$) | H | H |
| 219 | H | H | H | H | HO—CH$_2$\\CH—/HO—CH$_2$ | H | H | O(n-C$_3$H$_7$) | H | H |

TABLE 6-continued

| Exemplified Compound | R3 | R4 | R5 | R6 | R1 | R2 S1 | S2 | S3 | S4 | S5 |
|---|---|---|---|---|---|---|---|---|---|---|
| 220 | H | H | H | H | HO—CH₂\CH—/HO—CH₂ | H | H | N(C₂H₅)₂ | H | H |
| 221 | H | H | H | H | HO\CH-CH₂—/HO—CH₂ | CH(CH₃)₂ | H | H | H | CH(CH₃)₂ |
| 222 | H | H | H | H | HO\CH-CH₂—/HO—CH₂ | OCH₃ | H | H | OCH₃ | H |
| 223 | H | H | H | H | HO\CH-CH₂—/HO—CH₂ | C₂H₅ | H | H | H | C₂H₅ |

TABLE 7

| Exemplified Compound | R3 | R4 | R5 | R6 | R1 | R2 S1 | S2 | S3 | S4 | S5 |
|---|---|---|---|---|---|---|---|---|---|---|
| 224 | H | H | H | H | HO\CH-CH₂—/HO—CH₂ | H | H | CO(n-C₃H₇) | H | H |
| 225 | H | H | H | H | HO\CH-CH₂—/HO—CH₂ | H | H | N(C₂H₅)₂ | H | H |
| 226 | H | H | H | H | HO—C₂H₄\N—C₃H₆—/HO—C₂H₄ | CH(CH₃)₂ | H | H | H | CH(CH₃)₂ |
| 227 | H | H | H | H | HO—C₂H₄\N—C₃H₆—/HO—C₂H₄ | OCH₃ | H | H | OCH₃ | H |
| 228 | H | H | H | H | HO—CH₂\H₃C—C—/HO—CH₂ | CH(CH₃)₂ | H | H | H | CH(CH₃)₂ |
| 229 | H | H | H | H | HO—CH₂\CH—/HO—CH\Ph | CH(CH₃)₂ | H | H | H | CH(CH₃)₂ |
| 230 | CN | H | H | CN | HO—CH₂\CH—/HO—CH₂ | CH(CH₃)₂ | H | H | H | CH(CH₃)₂ |

TABLE 7-continued

| Exemplified Compound | R3 | R4 | R5 | R6 | R1 | R2 S1 | S2 | S3 | S4 | S5 |
|---|---|---|---|---|---|---|---|---|---|---|
| 231 | H | NO$_2$ | NO$_2$ | H | HO—CH$_2$\\CH—/HO—CH$_2$ | C$_2$H$_5$ | H | H | H | C$_2$H$_5$ |
| 232 | Br | H | H | Br | HO—CH$_2$\\CH—/HO—CH$_2$ | CH(CH$_3$)$_2$ | H | H | H | CH(CH$_3$)$_2$ |
| 233 | CH$_3$ | H | H | CH$_3$ | HO—CH$_2$\\CH—/HO—CH$_2$ | C$_2$H$_5$ | H | H | H | C$_2$H$_5$ |
| 234 | H | Cl | Cl | H | HO—CH$_2$\\CH—/HO—CH$_2$ | CH(CH$_3$)$_2$ | H | H | H | CH(CH$_3$)$_2$ |

TABLE 8

| Exemplified Compound | R3 | R4 | R5 | R6 | R1 | R2 S1 | S2 | S3 | S4 | S5 |
|---|---|---|---|---|---|---|---|---|---|---|
| 235 | H | H | H | H | HOOC\\CH—/HO—CH$_2$ | CH(CH$_3$)$_2$ | H | H | H | CH(CH$_3$)$_2$ |
| 236 | H | H | H | H | HOOC\\CH—/HO—CH$_2$ | OCH$_3$ | H | H | OCH$_3$ | H |
| 237 | H | H | H | H | HOOC\\CH—/HS—CH$_2$ | C$_2$H$_5$ | H | H | H | C$_2$H$_5$ |
| 238 | H | H | H | H | HOOC\\CH—/HS—CH$_2$ | OCH$_3$ | H | H | OCH$_3$ | H |
| 239 | H | H | H | H | HO\\CH-CH$_2$—/H$_2$N—CH$_2$ | CH(CH$_3$)$_2$ | H | H | H | CH(CH$_3$)$_2$ |
| 240 | H | H | H | H | HO\\CH-CH$_2$—/H$_2$N—CH$_2$ | OCH$_3$ | H | H | OCH$_3$ | H |
| 241 | H | H | H | H | HOOC\\CH—/HO—C$_2$H$_4$ | C$_2$H$_5$ | H | H | H | C$_2$H$_5$ |
| 242 | H | H | H | H | HOOC\\CH—/HS—C$_2$H$_4$ | CH(CH$_3$)$_2$ | H | H | H | CH(CH$_3$)$_2$ |

TABLE 8-continued

| Exemplified Compound | R3 | R4 | R5 | R6 | R1 | R2 | | | | |
|---|---|---|---|---|---|---|---|---|---|---|
| | | | | | | S1 | S2 | S3 | S4 | S5 |
| 243 | H | H | H | H | HOOC—CH(OH)—C₂H₄— | OCH₃ | H | H | OCH₃ | H |

TABLE 9

| Exemplified Compound | R3 | R4 | R5 | R6 | R1 | R2 | | | | |
|---|---|---|---|---|---|---|---|---|---|---|
| | | | | | | S1 | S2 | S3 | S4 | S5 |
| 244 | H | H | H | H | (HO—CH₂)₃C— | CH(CH₃)₂ | H | H | H | CH(CH₃)₂ |
| 245 | H | H | H | H | HOOC—CH(—)—CH(OH)—COOH | C₂H₅ | H | H | H | C₂H₅ |
| 246 | H | H | H | H | OHC—CH(—)—CH(OH)—CH(OH)—C₂H₄—OH | CH(CH₃)₂ | H | H | H | CH(CH₃)₂ |
| 247 | H | H | H | H | HO—CH₂—CH(OH)—CH(OH)—CH(OH)—CH(OH)—CH₂— | C₂H₅ | H | H | H | C₂H₅ |

TABLE 10

| Exemplified Compound | R3 | R4 | R5 | R6 | R1 | R2 | | | | |
|---|---|---|---|---|---|---|---|---|---|---|
| | | | | | | S1 | S2 | S3 | S4 | S5 |
| 248 | H | H | H | H | (HO—CH₂)₂CH— | n-C₃H₇ | H | H | H | H |
| 249 | H | H | H | H | (HO—CH₂)₂CH— | CH(CH₃)₂ | H | H | H | H |
| 250 | H | H | H | H | (HO—CH₂)₂CH— | CH₃ | CH₃ | H | H | H |
| 251 | H | H | H | H | (HO—CH₂)₂CH— | CH₃ | H | Br | H | CH₃ |

TABLE 10-continued

| Exemplified Compound | R3 | R4 | R5 | R6 | R1 | R2 S1 | S2 | S3 | S4 | S5 |
|---|---|---|---|---|---|---|---|---|---|---|
| 252 | H | H | H | H | (HO—CH$_2$)$_2$CH— | CF$_3$ | H | H | H | H |
| 253 | H | H | H | H | (HO—CH$_2$)$_2$CH— | COCH$_3$ | H | H | H | H |
| 254 | H | H | H | H | (HO—CH$_2$)$_2$CH— | COO(n-C$_4$H$_9$) | H | H | H | H |
| 255 | H | H | H | H | (HO—CH$_2$)$_2$CH— | COOCH$_3$ | H | COCH$_3$ | COCH$_3$ | H |
| 256 | H | H | H | H | (HO—CH$_2$)$_2$CH— | CH$_3$ | H | COCH$_3$ | H | H |
| 257 | H | H | H | H | (HO—CH$_2$)$_2$CH— | CH$_3$ | H | H | H | COOCH$_3$ |
| 258 | H | H | H | H | (HO—CH$_2$)$_2$CH— | OC$_2$H$_5$ | H | H | H | H |
| 259 | H | H | H | H | (HO—CH$_2$)$_2$CH— | OC$_2$H$_5$ | H | H | OC$_2$H$_5$ | H |
| 260 | H | H | H | H | (HO—CH$_2$)$_2$CH— | OCF$_3$ | H | H | H | H |
| 261 | H | H | H | H | (HO—CH$_2$)$_2$CH— | CH$_3$ | H | N(C$_2$H$_5$)$_2$ | H | H |
| 262 | H | H | H | H | (HO)(HO—CH$_2$)CH—CH$_2$— | n-C$_4$H$_9$ | H | H | H | H |
| 263 | H | H | H | H | (HO)(HO—CH$_2$)CH—CH$_2$— | CH(CH$_3$)$_2$ | H | H | H | H |
| 264 | H | H | H | H | (HO)(HO—CH$_2$)CH—CH$_2$— | CH$_3$ | H | H | H | COOCH$_3$ |

TABLE 10-continued

| Exemplified Compound | R3 | R4 | R5 | R6 | R1 | R2 S1 | S2 | S3 | S4 | S5 |
|---|---|---|---|---|---|---|---|---|---|---|
| 265 | H | H | H | H | HO—CH₂—CH(—)—CH₂—OH | OC₂H₅ | H | H | OC₂H₅ | H |
| 266 | H | H | H | H | HO—CH₂—CH(—)—CH₂—OH | OCF₃ | H | H | H | H |
| 267 | H | H | H | H | HO—CH₂—CH(—)—CH₂—OH | CH₃ | H | N(C₂H₅)₂ | H | H |

Tables 6 to 10 show cases where $R^2$ in the compound represented by the formula (1) represents a monovalent group represented by the formula (3).

A derivative having a structure represented by the formula (1) (derivative of the electron-transporting substance) may be synthesized using a known synthesis method disclosed in, for example, U.S. Pat. No. 4,442,193, U.S. Pat. No. 4,992,349, U.S. Pat. No. 5,468,583, or Chemistry of materials, Vol. 19, No. 11, 2703-2705 (2007), or may be synthesized through a reaction of naphthalenetetracarboxylic dianhydride that may be purchased from Tokyo Chemical Industry Co., Ltd., Sigma-Aldrich Japan K.K., and Johnson Matthey Japan Incorporated and a monoamine derivative.

The compound represented by the formula (1) has a polymerizable functional group (a hydroxy group, a thiol group, an amino group, or a carboxyl group) that can react with the crosslinking agent. Available as a method of introducing any such polymerizable functional group into the derivative having the structure represented by the formula (1) is a method involving directly introducing the polymerizable functional group into the derivative having the structure represented by the formula (1), or a method involving introducing a structure having the polymerizable functional group or a functional group that can serve as a precursor of the polymerizable functional group. Available as the latter method is a method involving introducing a functional group-containing aryl group by means of a cross-coupling reaction based on a halide of a naphthylimide derivative involving using a palladium catalyst and a base. Also available is a method involving introducing a functional group-containing alkyl group by means of a cross-coupling reaction based on the halide of the naphthylimide derivative involving using an $FeCl_3$ catalyst and a base. Also available is a method involving subjecting the halide of the naphthylimide derivative to lithiation, and causing an epoxy compound or $CO_2$ to act on the resultant to introduce a hydroxyalkyl group or a carboxyl group. Available is a method involving using, as a raw material in the synthesis of the naphthylimide derivative, a naphthalenetetracarboxylic dianhydride derivative or monoamine derivative having the polymerizable functional group or a functional group that can serve as a precursor of the polymerizable functional group.

An electrophotographic photosensitive member of the present invention is an electrophotographic photosensitive member including a support, an undercoat layer formed on the support, and a photosensitive layer formed on the undercoat layer. The electrophotographic photosensitive member preferably includes a laminated (separated-function) photosensitive layer separated into a charge-generating layer containing a charge-generating substance and a hole-transporting layer containing a hole-transporting substance. Further, the laminated photosensitive layer is preferably a forward-laminated photosensitive layer obtained by laminating the charge-generating layer and the hole-transporting layer in the stated order from a side closer to the support from the viewpoints of electrophotographic characteristics.

Figure 4A:
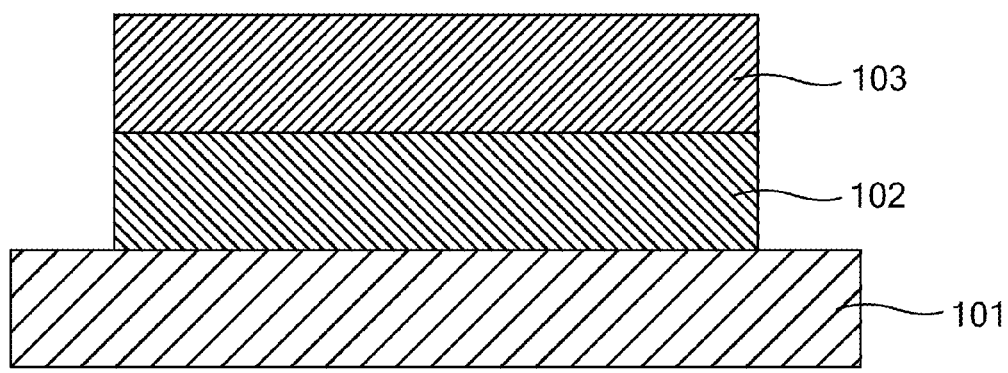
FIG. 4A is a view illustrating an example of the layer construction of the electrophotographic photosensitive member.
Figure 4B:
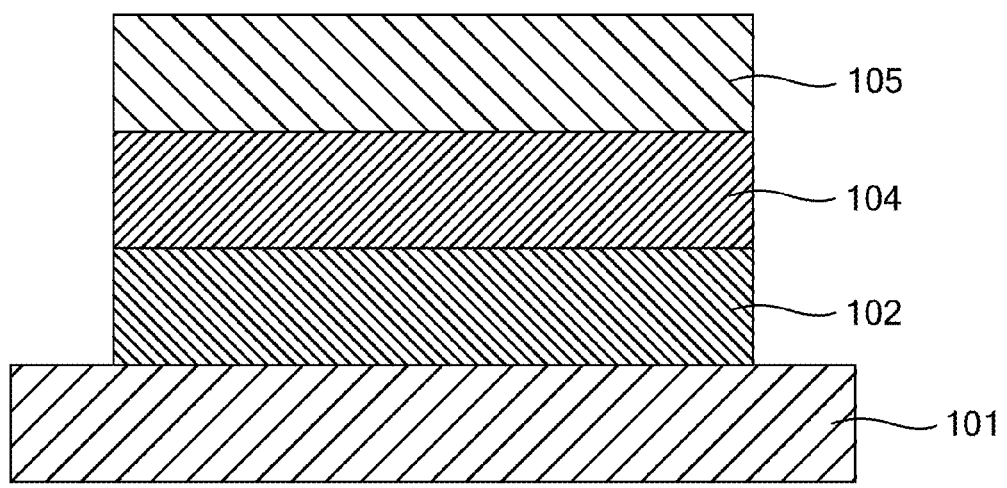
FIG. 4B is a view illustrating an example of the layer construction of the electrophotographic photosensitive member.

FIG. 4A and FIG. 4B are each a view illustrating an example of the layer construction of the electrophotographic photosensitive member. FIG. 4A illustrates a support 101, an undercoat layer 102 formed on the support 101, and a photosensitive layer 103 formed on the undercoat layer 102. In addition, FIG. 4B illustrates a charge-generating layer 104 formed on the undercoat layer and a hole-transporting layer 105 formed on the charge-generating layer.

Although a cylindrical electrophotographic photosensitive member obtained by forming the photosensitive layer (the charge-generating layer and the hole-transporting layer) on a cylindrical support has been widely used as a general electrophotographic photosensitive member, an electrophotographic photosensitive member of a shape such as a belt shape or a sheet shape can also be used.

[Support]

The support is preferably a support having conductivity (conductive support). For example, a support made of a metal such as aluminum, nickel, copper, gold, or iron, or an alloy thereof can be used. Given as an example thereof is a support obtained by forming a thin film of a metal such as aluminum, silver, or gold on an insulating support such as a polyester resin, a polycarbonate resin, a polyimide resin, or a glass. A support having formed thereon a thin film of a conductive material such as indium oxide or tin oxide is also given as an example thereof.

The surface of the support may be subjected to electrochemical treatment such as anodization, wet honing treatment, blast treatment, or cutting treatment in order that the electrical characteristics of the electrophotographic photosensitive member may be improved and interference fringes may be suppressed.

A conductive layer may be formed between the support and the undercoat layer to be described later. The conductive layer is obtained by: forming, on the support, a coating film of an application liquid for the conductive layer obtained by dispersing conductive particles in a resin; and drying the coating film.

Examples of the conductive particles include carbon black, acetylene black, powder of a metal such as aluminum, nickel, iron, nichrome, copper, zinc, or silver, and powder of a metal oxide such as conductive tin oxide or ITO.

In addition, examples of the resin include a polyester resin, a polycarbonate resin, a polyvinyl butyral resin, an acrylic resin, a silicone resin, an epoxy resin, a melamine resin, a urethane resin, a phenol resin, and an alkyd resin.

Examples of the solvent of the application liquid for the conductive layer include an ether-based solvent, an alcohol-based solvent, a ketone-based solvent, and an aromatic hydrocarbon solvent. The thickness of the conductive layer is preferably 0.2 µm or more and 40 µm or less, more preferably 1 µm or more and 35 µm or less, still more preferably 5 µm or more and 30 µm or less.

[Photosensitive Layer]

The photosensitive layer (the charge-generating layer and the hole-transporting layer) is formed on the undercoat layer. A plurality of charge-generating layers may be formed and a plurality of hole-transporting layers may also be formed.

Examples of the charge-generating substance include an azo pigment, a perylene pigment, an anthraquinone derivative, an anthanthrone derivative, a dibenzpyrenequinone derivative, a pyranthrone derivative, a quinone pigment, an indigoid pigment, a phthalocyanine pigment, and a perinone pigment. Of those, an azo pigment and a phthalocyanine pigment are preferred. Of the phthalocyanine pigments, oxytitanium phthalocyanine, chlorogallium phthalocyanine, and hydroxy gallium phthalocyanine are preferred.

As a binder resin to be used for the charge-generating layer in the case where the photosensitive layer is a laminated photosensitive layer, there are given, for example: a polymer and copolymer of a vinyl compound such as styrene, vinyl acetate, vinyl chloride, an acrylic acid ester, a methacrylic acid ester, vinylidene fluoride, or trifluoroethylene; polyvinyl alcohol, polyvinyl acetal, polycarbonate, polyester, polysulfone, polyphenylene oxide, polyurethane, a cellulose resin, a phenol resin, a melamine resin, a silicone resin, and an epoxy resin. Of those, polyester, polycarbonate, and polyvinyl acetal are preferred.

In the charge-generating layer, the ratio (charge-generating substance/binder resin) of the charge-generating substance to the binder resin falls within the range of preferably from 10/1 to 1/10, more preferably from 5/1 to 1/5. A solvent to be used in an application liquid for the charge-generating layer is, for example, an alcohol-based solvent, a ketone-based solvent, an ether-based solvent, an ester-based solvent, or an aromatic hydrocarbon solvent. The thickness of the charge-generating layer is preferably 0.05 µm or more and 5 µm or less.

Examples of the hole-transporting substance include a hydrazone compound, a styryl compound, a benzidine compound, a butadiene compound, an enamine compound, a triarylamine compound, and triphenylamine. Further examples thereof include polymers each having a group derived from any one of those compounds in its main chain or side chain.

Examples of the binder resin to be used for the hole-transporting layer include polyester, polycarbonate, polymethacrylic acid ester, polyarylate, polysulfone, and polystyrene. Of those, polycarbonate and polyarylate are preferred. In addition, it is preferred that the weight-average molecular weight (Mw) of any such binder resin fall within the range of from 10,000 to 300,000.

In the hole-transporting layer, the ratio (hole-transporting substance/binder resin) of the hole-transporting substance to the binder resin falls within the range of preferably from 10/5 to 5/10, more preferably from 10/8 to 6/10. The thickness of the hole-transporting layer is preferably 5 µm or more and 40 µm or less. A solvent to be used in an application liquid for the hole-transporting layer is, for example, an alcohol-based solvent, a ketone-based solvent, an ether-based solvent, an ester-based solvent, or an aromatic hydrocarbon solvent.

It should be noted that another layer such as a second undercoat layer free of the polymer of the present invention may be formed between the support and the undercoat layer or between the undercoat layer and the photosensitive layer.

In addition, a protective layer containing conductive particles or a hole-transporting substance and a binder resin may be formed on the photosensitive layer (the hole-transporting layer). An additive such as a lubricant may be further incorporated into the protective layer. In addition, the binder resin itself of the protective layer may be provided with conductivity or hole-transporting property, and in this case, the conductive particles or a hole-transporting substance except the binder resin may not be incorporated into the protective layer. In addition, the binder resin of the protective layer may be a thermoplastic resin, or may be a curable resin cured with heat, light, or a radiation (such as an electron beam).

Preferred as a method of forming each layer constituting the electrophotographic photosensitive member such as the undercoat layer, the charge-generating layer, or a hole-transporting layer is the following method: an application liquid obtained by dissolving and/or dispersing a material constituting each layer in a solvent is applied, and the resultant coating film is dried and/or cured to form the layer. A method of applying the application liquid is, for example, an immersion application method (immersion coating method), a spray coating method, a curtain coating method, or a spin coating method. Of those, an immersion application method is preferred from the viewpoints of efficiency and productivity.

[Process Cartridge and Electrophotographic Apparatus]

FIG. 1 illustrates the schematic construction of an electrophotographic apparatus including a process cartridge including an electrophotographic photosensitive member.

In FIG. 1, a cylindrical electrophotographic photosensitive member 1 is rotationally driven about an axis 2 in a direction indicated by an arrow at a predetermined peripheral speed. The surface (peripheral surface) of the electrophotographic photosensitive member 1 to be rotationally driven is charged to a predetermined positive or negative potential by a charging unit 3 (such as a contact-type primary charger or a noncontact-type primary charger). Next, the surface is exposed to exposure light (image exposure light) 4 from an exposing unit (not shown) such as slit exposure or laser beam scanning exposure. Thus, electrostatic latent images corresponding to the target image are sequentially formed on the surface of the electrophotographic photosensitive member 1.

Next, the electrostatic latent images formed on the surface of the electrophotographic photosensitive member 1 are developed with toner in the developer of a developing unit 5 to become toner images. The toner images formed on and carried by the surface of the electrophotographic photosensitive member 1 are sequentially transferred onto a transfer material P (such as paper) by a transfer bias from a transferring unit 6 (such as a transfer roller). It should be noted that the transfer material P is supplied from a transfer material-supplying unit (not shown) to a space (abutment portion) between the electrophotographic photosensitive member 1 and the transferring unit 6 in synchronization with the rotation of the electrophotographic photosensitive member 1.

The transfer material P onto which the toner images have been transferred is separated from the surface of the electrophotographic photosensitive member 1 and introduced into a fixing unit 8, where the images are fixed. Thus, the transfer material is printed out as an image-formed product (print or copy) to the outside of the apparatus.

The surface of the electrophotographic photosensitive member 1 after the transfer of the toner images is cleaned through the removal of a transfer residual developer (transfer residual toner) by a cleaning unit 7 (such as a cleaning blade). Next, the surface is subjected to antistatic treatment by pre-exposure light (not shown) from a pre-exposing unit (not shown), and is then repeatedly used in image formation. It should be noted that when the charging unit 3 is a contact charging unit using a charging roller as illustrated in FIG. 1, pre-exposure is not necessarily needed.

The following procedure may be adopted: two or more of the electrophotographic photosensitive member 1, the charging unit 3, the developing unit 5, the transferring unit 6, and the cleaning unit 7 are selected, stored in a container, and integrally bonded to constitute a process cartridge, and the process cartridge is removably mounted onto the main body of the electrophotographic apparatus. In FIG. 1, the electrophotographic photosensitive member 1, the charging unit 3, the developing unit 5, and the cleaning unit 7 are integrally supported to provide a cartridge, and the cartridge serves as a process cartridge 9 removably mounted onto the main body of the electrophotographic apparatus by using a guiding unit 10 such as the rail of the main body of the electrophotographic apparatus.

Hereinafter, the present invention is described in more detail by way of examples. It should be noted that the term "part(s)" in the examples means "part(s) by mass." First, the synthesis examples of the imide compound (electron-transporting substance) represented by the formula (1) are described. The measurement of a NMR spectrum was performed under the following conditions. Measuring device used: (JMN-EX400 manufactured by JEOL Ltd.)
Solvent: Deuterated chloroform ($CDCl_3$)

Synthesis Example 1

Figure 5:
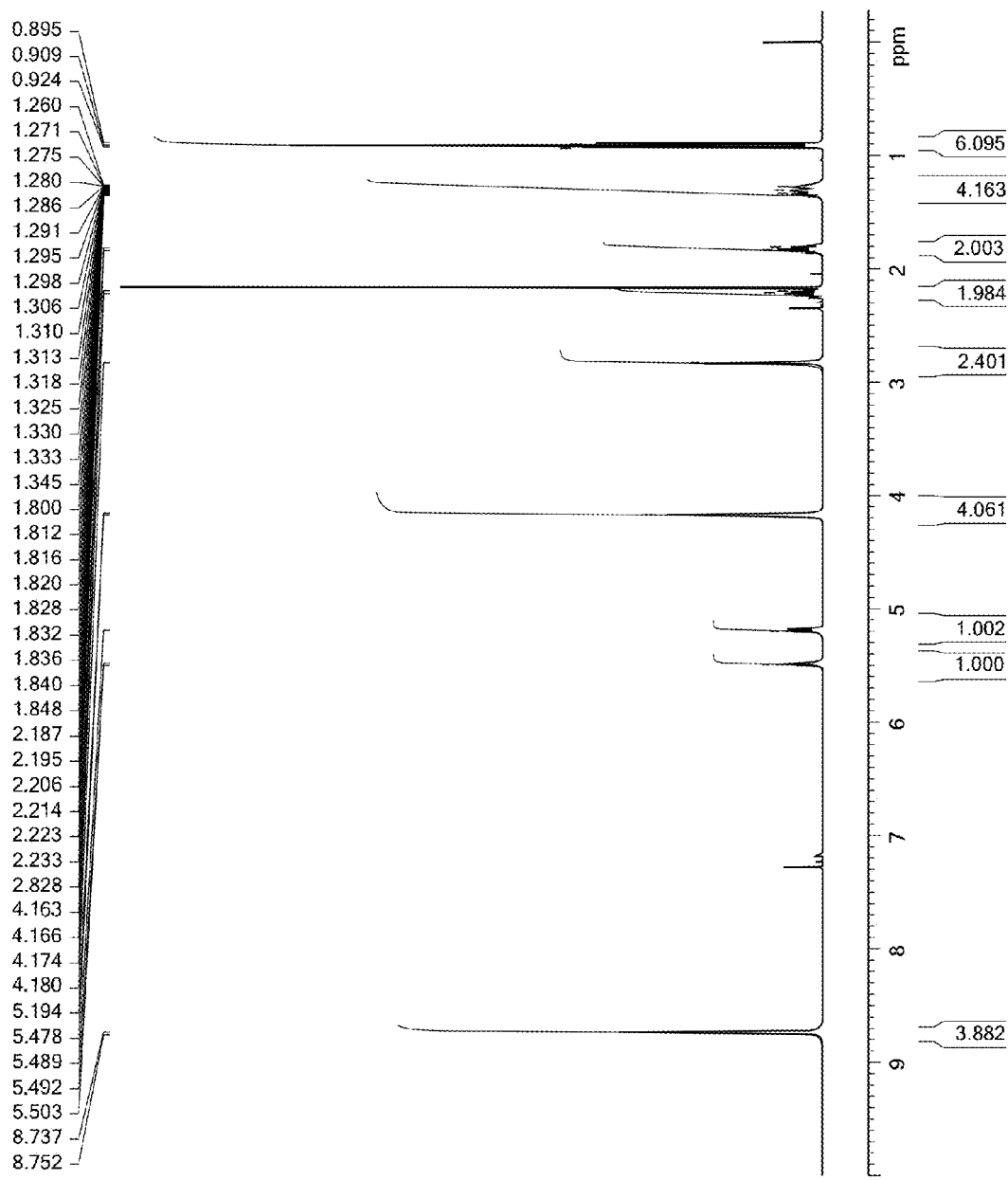
FIG. 5 is a graph showing the NMR spectrum of the compound of Synthesis Example 1.

Under a nitrogen atmosphere, 5.4 parts of naphthalenetetracarboxylic dianhydride, 4 parts of 4-heptylamine, and 3 parts of 2-amino-1,3-propanediol were added to 200 parts of dimethylacetamide, and the mixture was stirred at room temperature for 1 hour to prepare a solution. After having been prepared, the solution was refluxed for 8 hours and separated by silica gel column chromatography (developing solvent: ethyl acetate/toluene). After that, a fraction containing the target product was concentrated. The concentrate was recrystallized with a mixed solution of ethyl acetate and toluene to provide 2.0 parts of the target compound. The NMR spectrum of the resultant compound was measured with a nuclear magnetic resonance apparatus. As a result, the compound was found to be Exemplified Compound 101. FIG. 5 shows its NMR spectrum.

Synthesis Example 2

Figure 6:
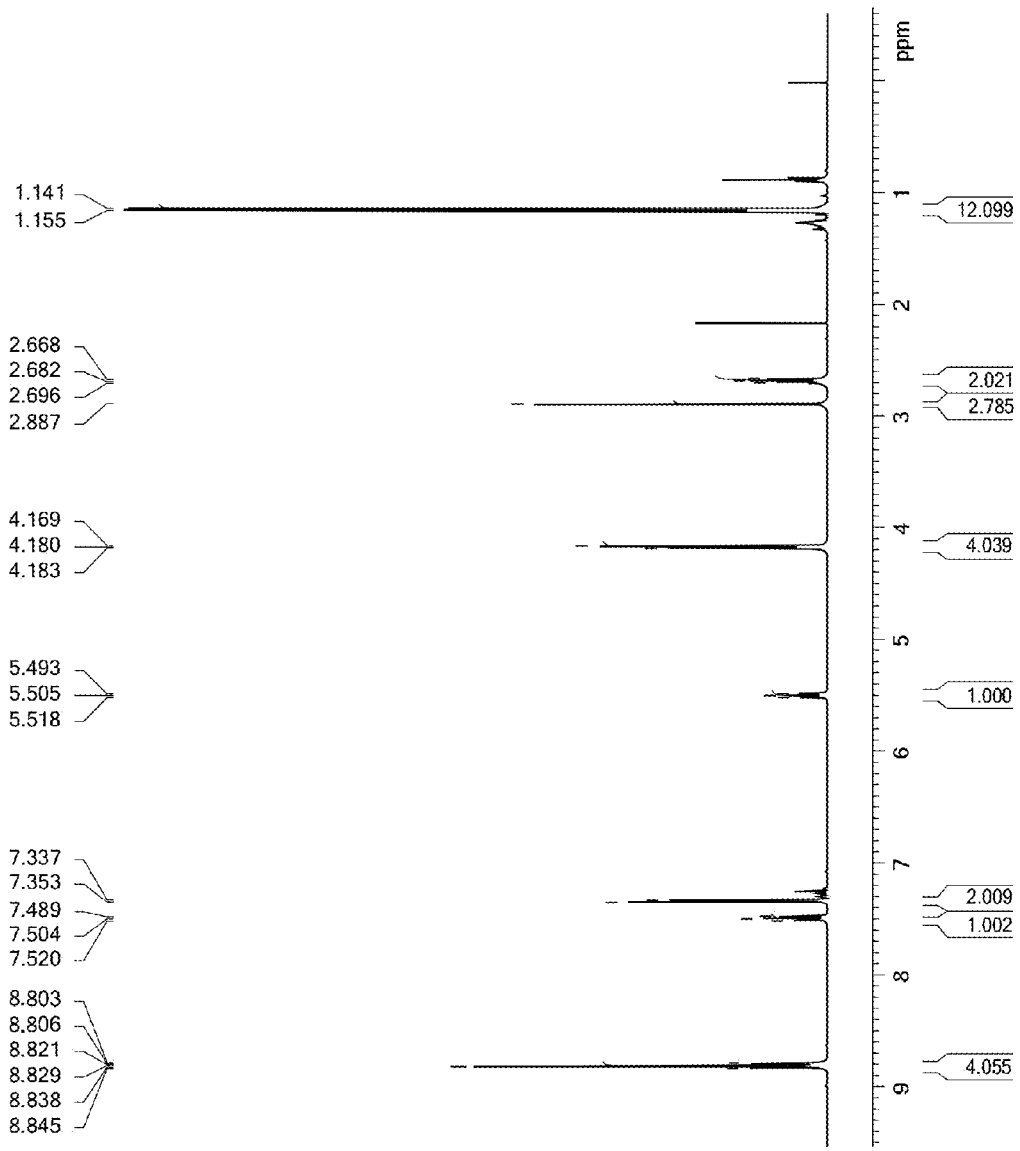
FIG. 6 is a graph showing the NMR spectrum of the compound of Synthesis Example 2.

Under a nitrogen atmosphere, 5.4 parts of naphthalenetetracarboxylic dianhydride, 4 parts of 2,6-diisopropylaniline, and 3 parts of 2-amino-1,3-propanediol were added to 200 parts of dimethylacetamide, and the mixture was stirred at room temperature for 1 hour to prepare a solution. After having been prepared, the solution was refluxed for 10 hours and separated by silica gel column chromatography (developing solvent: ethyl acetate/toluene). After that, a fraction containing the target product was concentrated. The concentrate was recrystallized with a mixed solution of ethyl acetate and toluene to provide 1.5 parts of the target compound. The NMR spectrum of the resultant compound was measured with a nuclear magnetic resonance apparatus. As a result, the compound was found to be Exemplified Compound 202. FIG. 6 shows its NMR spectrum.

Next, the production and evaluation of an electrophotographic photosensitive member are described.

Example 1

An aluminum cylinder having a length of 260.5 mm and a diameter of 30 mm (JIS-A3003, aluminum alloy) was used as a support (conductive support).

Next, 214 parts of titanium oxide ($TiO_2$) particles coated with oxygen-deficient tin oxide ($SnO_2$) as metal oxide particles, 132 parts of a phenol resin (trade name: PRIOPHEN J-325, manufactured by DIC Corporation, resin solid content: 60 mass %), and 98 parts of 1-methoxy-2-propanol were loaded into a sand mill using 450 parts of glass beads each having a diameter of 0.8 mm, and the mixture was subjected to dispersion treatment under the following conditions: a number of rotations of 2,000 rpm, a dispersion treatment time of 4.5 hours, and a preset temperature of cooling water of 18° C. Thus, a dispersion liquid was prepared. The glass beads were removed from the dispersion liquid with a mesh (aperture: 150 μm).

Silicone resin particles were added to the dispersion liquid after the removal of the glass beads so that their content became 10 mass % with respect to the total mass of the metal oxide particles and binder resin in the dispersion liquid. In addition, a silicone oil was added to the dispersion liquid so that its content became 0.01 mass % with respect to the total mass of the metal oxide particles and binder resin in the dispersion liquid, followed by stirring. Thus, an application liquid for a conductive layer was prepared. The application liquid for a conductive layer was applied onto the support by immersion to form a coating film, and the resultant coating film was dried and thermally cured for 30 minutes at 150° C. to form a conductive layer having a thickness of 30 μm. TOSPEARL 120 (average particle diameter: 2 μm) manufactured by Momentive Performance Materials Inc. was used as the silicone resin particles. SH28PA manufactured by Dow Corning Toray Co., Ltd. was used as the silicone oil.

Next, 4 parts of Exemplified Compound (101), 1.5 parts of a polyvinyl butyral resin (trade name: BX-1, manufactured by SEKISUI CHEMICAL CO., LTD.), and 0.0005 part of zinc(II) octylate as a catalyst were dissolved in a mixed solvent of 100 parts of dimethylacetamide and 100 parts of tetrahydrofuran. A blocked isocyanate (trade name: BL3175, manufactured by Sumika Bayer) corresponding to a solid content of 6 parts was added to the solution to prepare an application liquid for an undercoat layer. The application liquid for an undercoat layer was applied onto the conductive layer by immersion to form a coating film, and the resultant coating film was thermally cured for 40 minutes at 160° C. to form an undercoat layer having a thickness of 1.5 μm.

Next, a hydroxygallium phthalocyanine crystal (charge-generating substance) of a crystal form having peaks at Bragg angles)(2θ±0.2° in CuKα characteristic X-ray diffraction of 7.5°, 9.9°, 12.5°, 16.3°, 18.6°, 25.1°, and 28.3° was prepared. 10 Parts of the hydroxygallium phthalocyanine crystal, 5 parts of a polyvinyl butyral resin (trade name: S-LEC BX-1, manufactured by SEKISUI CHEMICAL CO., LTD.), and 250 parts of cyclohexanone were loaded into a sand mill using glass beads each having a diameter of 1 mm, and the mixture was subjected to dispersion treatment for 2 hours. Next, 250 parts of ethyl acetate were added to the resultant to prepare an application liquid for a charge-generating layer. The application liquid for a charge-generating layer was applied onto the undercoat layer by immersion to form a coating film, and the resultant coating film was dried for minutes at a temperature of 95° C. to form a charge-generating layer having a thickness of 0.15 µm.

Next, 8 parts of an amine compound (hole-transporting substance) represented by the following formula (4) and 10 parts of a polyarylate resin having a structural unit represented by the following formula (5) were dissolved in a mixed solvent of 40 parts of dimethoxymethane and 60 parts of chlorobenzene to prepare an application liquid for a hole-transporting layer. The polyarylate resin had a weight-average molecular weight (Mw) of 100,000. The application liquid for a hole-transporting layer was applied onto the charge-generating layer by immersion to form a coating film, and the resultant coating film was dried for 40 minutes at a temperature of 120° C. to form a hole-transporting layer having a thickness of 15 µm.

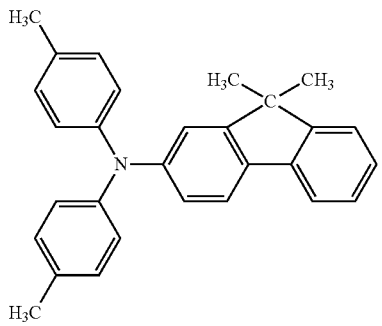

(4)

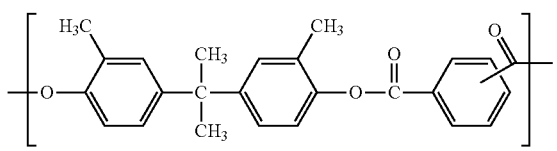

(5)

Thus, an electrophotographic photosensitive member including, on the support, the conductive layer, the undercoat layer, the charge-generating layer, and the hole-transporting layer was produced.

The produced electrophotographic photosensitive member was mounted onto a reconstructed machine of a laser beam printer (trade name: LBP-2510) manufactured by Canon Inc. under an environment having a temperature of 23° C. and a humidity of 50% RH, followed by the measurement of its surface potential and the evaluation of an output image. The printer was reconstructed as follows: primary charging was changed to roller contact DC charging, its process speed was changed to 120 mm/sec, and laser exposure was performed. Details about the foregoing are as described below.

(Measurement of Surface Potential)

The process cartridge for a cyan color of the laser beam printer was reconstructed and a potential probe (model 6000B-8: manufactured by TREK JAPAN) was mounted at a development position. Then, a potential at the central portion of the electrophotographic photosensitive member was measured with a surface potentiometer (model 344: manufactured by TREK JAPAN). During the measurement of the surface potential of the electrophotographic photosensitive member, the light quantity of image exposure was set so that an initial dark portion potential (Vd) became −600 V and an initial light portion potential (Vl) became −150 V.

Subsequently, the produced electrophotographic photosensitive member was mounted onto the process cartridge for a cyan color of the laser beam printer, and the process cartridge was mounted onto a cyan process cartridge station, followed by the output of an image. First, one solid white image, five images for a ghost evaluation, one solid black image, and five images for a ghost evaluation were continuously output in the stated order.

Figure 3:
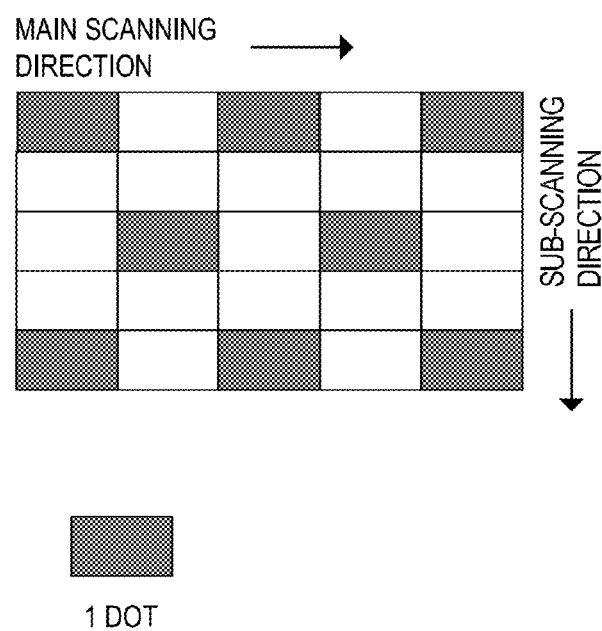
FIG. 3 is a view illustrating a one-dot knight-jump pattern image.
Figure 2:
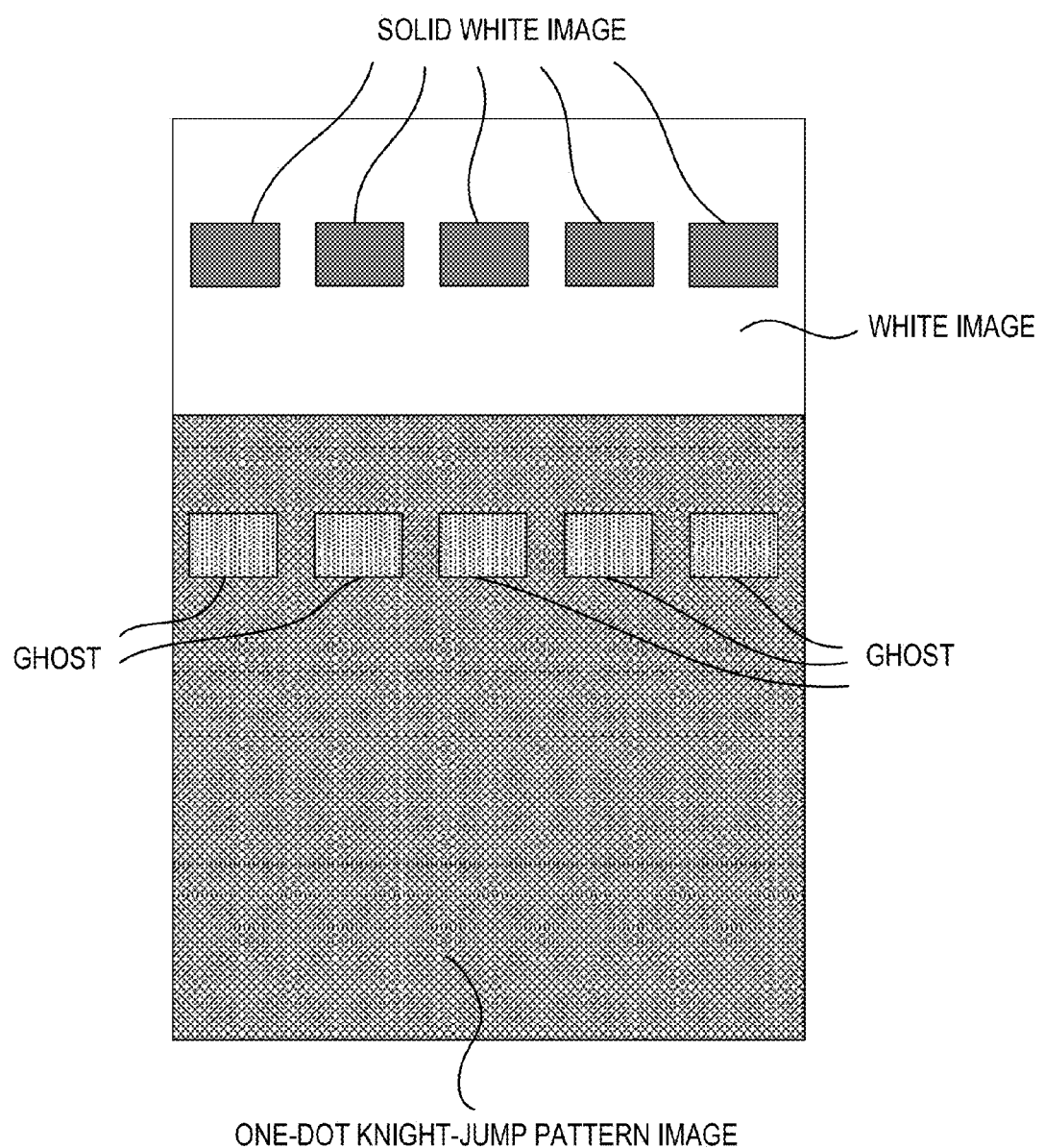
FIG. 2 is a view illustrating a print for a ghost evaluation to be used at the time of a ghost image evaluation.

Each image for a ghost evaluation is obtained by: outputting a quadrangular "solid image" in a "white image" at the leading end of an image as illustrated in FIG. 2; and producing a "halftone image of a one-dot knight-jump pattern" illustrated in FIG. 3 after the output. It should be noted that a "ghost" portion in FIG. 2 is a portion where a ghost resulting from the "solid image" may appear.

An evaluation for a positive ghost was performed by measuring a difference between the image density of the halftone image of a one-dot knight-jump pattern and the image density of the ghost portion. The density difference was measured at ten sites in one image for a ghost evaluation with a spectral densitometer (trade name: X-Rite 504/508, manufactured by X-Rite). The operation was performed for all of the ten images for a ghost evaluation, and the average of a total of 100 measured values was calculated. Table 11 shows the result. As the density difference (Macbeth density difference) enlarges, the positive ghost occurs more strongly. The fact that the density difference (Macbeth density difference) reduces means that the positive ghost is suppressed.

Examples 2 to 77

Electrophotographic photosensitive members were produced in the same manner as in Example 1 except that the kinds and contents of the compound represented by the formula (1), the crosslinking agent, and the resin having a polymerizable functional group were changed as shown in Tables 11 and 12, and evaluations for ghosts were similarly performed. Tables 11 and 12 show the results.

Comparative Example 1

An electrophotographic photosensitive member was produced in the same manner as in Example 1 except that the following application liquid for an undercoat layer was used, and an evaluation for a ghost was similarly performed. Table 12 shows the result.

3 Parts of a compound represented by the following formula (6) and 7 parts of a polyamide resin (AMILAN CM8000, manufactured by Toray Industries, Inc.) were dissolved in a mixed solvent of 120 parts of butanol, 100 parts of methanol, and 30 parts of dimethylformamide (DMF) to prepare an application liquid for an undercoat layer.

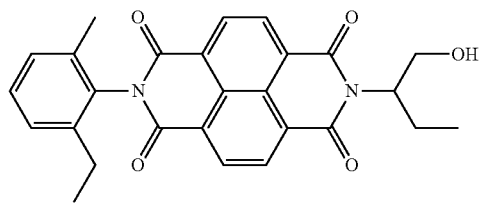

(6)

Comparative Example 2

An electrophotographic photosensitive member was produced in the same manner as in Example 1 except that the following application liquid for an undercoat layer was used, and an evaluation for a ghost was similarly performed. Table 12 shows the result.

5 Parts of a compound represented by the following formula (7) and 5 parts of a polyamide resin (AMILAN CM8000) were dissolved in a mixed solvent of 120 parts of butanol, 100 parts of methanol, and 30 parts of DMF to prepare an application liquid for an undercoat layer.

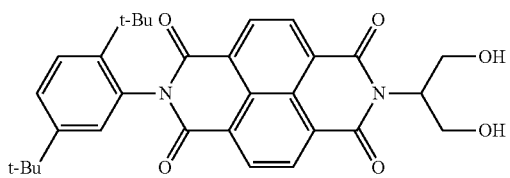

(7)

Comparative Example 3

An electrophotographic photosensitive member was produced in the same manner as in Example 1 except that the following application liquid for an undercoat layer was used, and an evaluation for a ghost was similarly performed. Table 12 shows the result.

10 Parts of a compound represented by the following formula (8) and 5 parts of a phenol resin (PL-4804, manufactured by Gun Ei Chemical Industry Co., Ltd.) were dissolved in a mixed solvent of 200 parts of dimethylformamide and 150 parts of benzyl alcohol to prepare an application liquid for an undercoat layer.

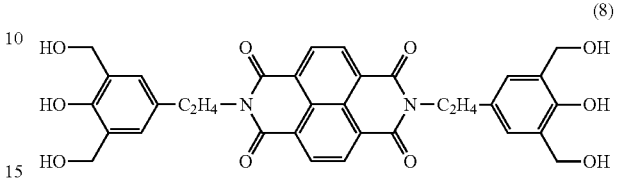

(8)

<Elution Test>

0.5 Gram of the application liquid for an undercoat layer prepared in each of Examples 1 to 77 was uniformly applied onto an aluminum sheet by a wire bar method, and the resultant coating film was heated and polymerized (cured) at a temperature of 160° C. for 30 minutes to provide a sample. Only a region measuring 100 mm by 50 mm was cut out of the central portion of the sample, and was immersed in a mixed liquid of anone and ethyl acetate each having a temperature of 20° C. (weight ratio=1:1) for 10 minutes, and its initial weight before the immersion and its weight after the immersion were measured. Further, the coating film formed on the sample was shaved off and the weight of the aluminum sheet was measured. A weight reduction ratio after the immersion (elution amount, %) was determined from the following equation.

Weight reduction ratio after immersion (%)=((initial weight−weight after immersion)/(initial weight−weight of aluminum sheet))×100

When the weight reduction ratio after the immersion (%) was 5% or less, the undercoat layer was judged to be a film that was hardly eluted. As a result, the undercoat layers formed in Examples 1 to 77 were each found to be a film that had a weight reduction ratio after the immersion (%) of 5% or less and was hardly eluted.

TABLE 11

| Example | Compound Kind of compound | Compound Constituent ratio | Crosslinking agent Kind of crosslinking agent | Crosslinking agent Constituent ratio | Resin Kind of resin | Resin Constituent ratio | Macbeth density difference Initial stage | Macbeth density difference Change after endurance |
|---|---|---|---|---|---|---|---|---|
| 1 | 101 | 100 | Crosslinking agent 1 | 150 | Resin 1 | 3.75 | 0.020 | 0.002 |
| 2 | 104 | 100 | Crosslinking agent 1 | 150 | Resin 1 | 3.75 | 0.023 | 0.004 |
| 3 | 118 | 100 | Crosslinking agent 1 | 150 | Resin 1 | 3.75 | 0.025 | 0.003 |
| 4 | 127 | 100 | Crosslinking agent 1 | 150 | Resin 1 | 3.75 | 0.025 | 0.005 |
| 5 | 132 | 100 | Crosslinking agent 3 | 150 | Resin 2 | 3.75 | 0.026 | 0.005 |
| 6 | 134 | 100 | Crosslinking agent 3 | 150 | Resin 2 | 3.75 | 0.029 | 0.008 |
| 7 | 136 | 100 | Crosslinking agent 3 | 150 | Resin 3 | 3.75 | 0.027 | 0.006 |
| 8 | 116 | 100 | Crosslinking agent 1 | 150 | Resin 1 | 3.75 | 0.031 | 0.010 |
| 9 | 117 | 100 | Crosslinking agent 1 | 150 | Resin 1 | 3.75 | 0.033 | 0.012 |
| 10 | 121 | 100 | Crosslinking agent 1 | 150 | Resin 1 | 3.75 | 0.039 | 0.009 |
| 11 | 123 | 100 | Crosslinking agent 2 | 150 | Resin 2 | 3.75 | 0.035 | 0.015 |
| 12 | 125 | 100 | Crosslinking agent 2 | 150 | Resin 2 | 3.75 | 0.038 | 0.014 |
| 13 | 138 | 100 | Crosslinking agent 3 | 150 | Resin 2 | 3.75 | 0.038 | 0.011 |
| 14 | 142 | 100 | Crosslinking agent 3 | 150 | Resin 2 | 3.75 | 0.033 | 0.013 |
| 15 | 143 | 100 | Crosslinking agent 1 | 150 | Resin 3 | 3.75 | 0.035 | 0.013 |
| 16 | 133 | 100 | Crosslinking agent 3 | 150 | Resin 3 | 3.75 | 0.038 | 0.009 |
| 17 | 101 | 100 | Crosslinking agent 1 | 212 | Resin 1 | 38 | 0.027 | 0.010 |
| 18 | 101 | 100 | Crosslinking agent 1 | 30 | Resin 1 | 20 | 0.023 | 0.015 |
| 19 | 101 | 100 | Crosslinking agent 1 | 150 | — | — | 0.035 | 0.013 |
| 20 | 101/104 | 50/50 | Crosslinking agent 1 | 150 | Resin 1 | 3.75 | 0.020 | 0.001 |
| 21 | 101/132 | 50/50 | Crosslinking agent 3 | 150 | Resin 1 | 3.75 | 0.023 | 0.002 |

TABLE 11-continued

| | Compound | | Crosslinking agent | | Resin | | Macbeth density difference | |
|---|---|---|---|---|---|---|---|---|
| Example | Kind of compound | Constituent ratio | Kind of cross-linking agent | Constituent ratio | Kind of resin | Constituent ratio | Initial stage | Change after endurance |
| 22 | 132 | 100 | Crosslinking agent 1/ Crosslinking agent 3 | 50/100 | Resin 1 | 3.75 | 0.023 | 0.005 |
| 23 | 202 | 100 | Crosslinking agent 1 | 150 | Resin 2 | 3.75 | 0.021 | 0.002 |
| 24 | 204 | 100 | Crosslinking agent 1 | 150 | Resin 2 | 3.75 | 0.022 | 0.005 |
| 25 | 221 | 100 | Crosslinking agent 2 | 150 | Resin 1 | 3.75 | 0.024 | 0.003 |
| 26 | 230 | 100 | Crosslinking agent 1 | 150 | Resin 1 | 3.75 | 0.022 | 0.005 |
| 27 | 235 | 100 | Crosslinking agent 3 | 150 | Resin 1 | 3.75 | 0.027 | 0.008 |
| 28 | 237 | 100 | Crosslinking agent 4 | 150 | Resin 3 | 3.75 | 0.029 | 0.005 |
| 29 | 239 | 100 | Crosslinking agent 4 | 150 | Resin 3 | 3.75 | 0.023 | 0.003 |
| 30 | 218 | 100 | Crosslinking agent 1 | 150 | Resin 1 | 3.75 | 0.031 | 0.009 |
| 31 | 225 | 100 | Crosslinking agent 1 | 150 | Resin 1 | 3.75 | 0.033 | 0.015 |
| 32 | 226 | 100 | Crosslinking agent 1 | 150 | Resin 1 | 3.75 | 0.038 | 0.013 |
| 33 | 243 | 100 | Crosslinking agent 3 | 150 | Resin 1 | 3.75 | 0.035 | 0.014 |
| 34 | 244 | 100 | Crosslinking agent 1 | 150 | Resin 3 | 3.75 | 0.032 | 0.010 |
| 35 | 247 | 100 | Crosslinking agent 2 | 150 | Resin 3 | 3.75 | 0.038 | 0.011 |
| 36 | 202 | 100 | Crosslinking agent 1 | 212 | Resin 1 | 38 | 0.025 | 0.010 |
| 37 | 202 | 100 | Crosslinking agent 1 | 30 | Resin 1 | 20 | 0.024 | 0.013 |
| 38 | 202 | 100 | Crosslinking agent 1 | 150 | — | — | 0.039 | 0.015 |
| 39 | 202/204 | 50/50 | Crosslinking agent 1 | 150 | Resin 1 | 3.75 | 0.022 | 0.001 |
| 40 | 202/235 | 50/50 | Crosslinking agent 3 | 150 | Resin 1 | 3.75 | 0.025 | 0.005 |
| 41 | 235 | 100 | Crosslinking agent 1/ Crosslinking agent 3 | 50/100 | Resin 1 | 3.75 | 0.027 | 0.003 |
| 42 | 101 | 100 | Crosslinking agent 3 | 150 | Resin 1 | 3.75 | 0.022 | 0.002 |
| 43 | 102 | 100 | Crosslinking agent 1 | 150 | Resin 1 | 3.75 | 0.021 | 0.005 |
| 44 | 102 | 100 | Crosslinking agent 3 | 150 | Resin 1 | 3.75 | 0.026 | 0.004 |
| 45 | 106 | 100 | Crosslinking agent 1 | 150 | Resin 1 | 3.75 | 0.027 | 0.006 |
| 46 | 107 | 100 | Crosslinking agent 1 | 150 | Resin 1 | 3.75 | 0.022 | 0.004 |
| 47 | 110 | 100 | Crosslinking agent 1 | 150 | Resin 1 | 3.75 | 0.025 | 0.008 |
| 48 | 111 | 100 | Crosslinking agent 1 | 150 | Resin 1 | 3.75 | 0.021 | 0.006 |
| 49 | 119 | 100 | Crosslinking agent 1 | 150 | Resin 1 | 3.75 | 0.023 | 0.005 |
| 50 | 145 | 100 | Crosslinking agent 1 | 150 | Resin 1 | 3.75 | 0.027 | 0.003 |
| 51 | 146 | 100 | Crosslinking agent 1 | 150 | Resin 1 | 3.75 | 0.028 | 0.007 |
| 52 | 147 | 100 | Crosslinking agent 1 | 150 | Resin 1 | 3.75 | 0.023 | 0.003 |
| 53 | 148 | 100 | Crosslinking agent 1 | 150 | Resin 1 | 3.75 | 0.023 | 0.003 |
| 54 | 149 | 100 | Crosslinking agent 1 | 150 | Resin 1 | 3.75 | 0.025 | 0.002 |
| 55 | 151 | 100 | Crosslinking agent 1 | 150 | Resin 1 | 3.75 | 0.025 | 0.007 |
| 56 | 155 | 100 | Crosslinking agent 1 | 150 | Resin 1 | 3.75 | 0.028 | 0.004 |
| 57 | 156 | 100 | Crosslinking agent 1 | 150 | Resin 1 | 3.75 | 0.027 | 0.006 |
| 58 | 158 | 100 | Crosslinking agent 1 | 150 | Resin 1 | 3.75 | 0.025 | 0.006 |
| 59 | 159 | 100 | Crosslinking agent 1 | 150 | Resin 1 | 3.75 | 0.023 | 0.005 |
| 60 | 160 | 100 | Crosslinking agent 1 | 150 | Resin 1 | 3.75 | 0.022 | 0.004 |
| 61 | 161 | 100 | Crosslinking agent 1 | 150 | Resin 1 | 3.75 | 0.023 | 0.008 |
| 62 | 162 | 100 | Crosslinking agent 1 | 150 | Resin 1 | 3.75 | 0.024 | 0.006 |
| 63 | 202 | 100 | Crosslinking agent 3 | 150 | Resin 1 | 3.75 | 0.024 | 0.003 |
| 64 | 203 | 100 | Crosslinking agent 1 | 150 | Resin 1 | 3.75 | 0.022 | 0.004 |
| 65 | 205 | 100 | Crosslinking agent 1 | 150 | Resin 1 | 3.75 | 0.025 | 0.006 |
| 66 | 208 | 100 | Crosslinking agent 1 | 150 | Resin 1 | 3.75 | 0.029 | 0.003 |
| 67 | 223 | 100 | Crosslinking agent 1 | 150 | Resin 1 | 3.75 | 0.024 | 0.007 |
| 68 | 248 | 100 | Crosslinking agent 1 | 150 | Resin 1 | 3.75 | 0.023 | 0.007 |
| 69 | 249 | 100 | Crosslinking agent 1 | 150 | Resin 1 | 3.75 | 0.026 | 0.005 |
| 70 | 250 | 100 | Crosslinking agent 1 | 150 | Resin 1 | 3.75 | 0.026 | 0.006 |
| 71 | 253 | 100 | Crosslinking agent 1 | 150 | Resin 1 | 3.75 | 0.023 | 0.003 |
| 72 | 254 | 100 | Crosslinking agent 1 | 150 | Resin 1 | 3.75 | 0.028 | 0.004 |
| 73 | 255 | 100 | Crosslinking agent 1 | 150 | Resin 1 | 3.75 | 0.026 | 0.006 |
| 74 | 257 | 100 | Crosslinking agent 1 | 150 | Resin 1 | 3.75 | 0.025 | 0.002 |
| 75 | 259 | 100 | Crosslinking agent 1 | 150 | Resin 1 | 3.75 | 0.023 | 0.003 |
| 76 | 260 | 100 | Crosslinking agent 1 | 150 | Resin 1 | 3.75 | 0.024 | 0.003 |
| 77 | 261 | 100 | Crosslinking agent 1 | 150 | Resin 1 | 3.75 | 0.023 | 0.005 |

TABLE 12

| | Compound | | Crosslinking agent | | Resin | | Macbeth density difference | |
|---|---|---|---|---|---|---|---|---|
| Comparative Example | Kind of compound | Constituent ratio | Kind of cross-linking agent | Constituent ratio | Kind of resin | Constituent ratio | Initial stage | Change after endurance |
| 1 | Compound (6) | 100 | — | — | Polyamide resin | 233 | 0.032 | 0.043 |
| 2 | Compound (7) | 100 | — | — | Polyamide resin | 100 | 0.037 | 0.055 |

TABLE 12-continued

| | Compound | | Crosslinking agent | | Resin | | Macbeth density difference | |
|---|---|---|---|---|---|---|---|---|
| Comparative Example | Kind of compound | Constituent ratio | Kind of crosslinking agent | Constituent ratio | Kind of resin | Constituent ratio | Initial stage | Change after endurance |
| 3 | Compound (8) | 100 | — | — | Phenol resin | 50 | 0.042 | 0.052 |

In Tables 11 and 12, the crosslinking agent 1 is an isocyanate-based crosslinking agent (trade name: DESMODUR BL3175, manufactured by Sumika Bayer Urethane (solid content: 60%)), the crosslinking agent 2 is an isocyanate-based crosslinking agent (trade name: DESMODUR BL3575, manufactured by Sumika Bayer Urethane (solid content: 60%)), the crosslinking agent 3 is a butylated melamine-based crosslinking agent (trade name: SUPER BECKAMINE J821-60, manufactured by DIC Corporation (solid content: 60%)), and the crosslinking agent 4 is a butylated urea-based crosslinking agent (trade name: BECKAMINE P138, manufactured by DIC Corporation (solid content: 60%)).

In Tables 11 and 12, the resin 1 (resin having a polymerizable functional group) is a polyvinyl acetal resin having a number of moles of a hydroxy group per 1 g of 3.3 mmol and a molecular weight of $1 \times 10^5$, the resin 2 is a polyvinyl acetal resin having a number of moles of a hydroxy group per 1 g of 3.3 mmol and a molecular weight of $2 \times 10^4$, and the resin 3 is a polyvinyl acetal resin having a number of moles of a hydroxy group per 1 g of 2.5 mmol and a molecular weight of $3.4 \times 10^5$.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-269676, filed Dec. 26, 2013, Japanese Patent Application No. 2014-079018, filed Apr. 7, 2014 and Japanese Patent Application No. 2014-246835, filed Dec. 5, 2014 which are hereby incorporated by reference herein in their entirety.

What is claimed is:

1. An electrophotographic photosensitive member, comprising:
   a support;
   an undercoat layer on the support; and
   a photosensitive layer on the undercoat layer,
   wherein the undercoat layer comprises a polymerized product of a composition comprising a compound represented by the following formula (1):

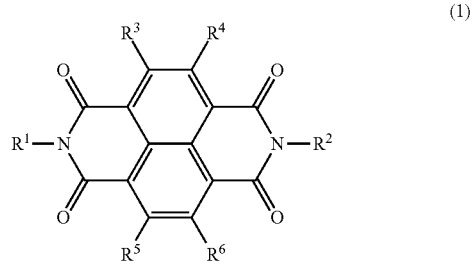

(1)

wherein,
$R^1$ represents an alkyl group having 1 to 6 main-chain carbon atoms and having two or more polymerizable functional groups, a group derived from one of $CH_2$ in the main chain of the alkyl group having 1 to 6 main-chain carbon atoms substituted for an oxygen atom and having two or more polymerizable functional groups, or a group derived from one of $CH_2$ in the main chain of the alkyl group having 1 to 6 main-chain carbon atoms substituted for $NR^7$ and having two or more polymerizable functional groups;

the polymerizable functional groups is a hydroxy group, a thiol group, an amino group, or a carboxyl group;

$R^7$ represents a hydrogen atom or an alkyl group;

$R^2$ represents an unsubstituted or substituted alkyl group having 1 to 6 main-chain carbon atoms, a group having 1 to 6 main chain atoms and derived from one of $CH_2$ in a main chain of an unsubstituted or substituted alkyl group substituted for an oxygen atom, a group having 1 to 6 main chain atoms and derived from one of $CH_2$ in the main chain of an unsubstituted or substituted alkyl group substituted for $NR^8$, or a substituted aryl group, and $R^8$ represents a hydrogen atom or an alkyl group;

a substituent of the substituted alkyl group is an alkyl group having 1 to 6 carbon atoms, a benzyl group, an alkoxycarbonyl group, or a phenyl group;

a substituent of the substituted aryl group is a halogen atom, a cyano group, a nitro group, a methyl group, an ethyl group, an isopropyl group, a n-propyl group, a n-butyl group, an acyl group, an alkoxycarbonyl group, an alkoxy group, a thioalkoxy group, or an aminoalkoxy group, and an atomic number of all substituent except for hydrogen atoms, which the aryl group has, is 4 or more; and $R^3$ to $R^6$ each independently represent a hydrogen atom, a halogen atom, a cyano group, a nitro group, an unsubstituted or substituted alkyl group, or an unsubstituted or substituted aryl group.

2. An electrophotographic photosensitive member according to claim 1, wherein $R^1$ represents an alkyl group having 1 to 3 main-chain carbon atoms and having two or more polymerizable functional groups, a group derived from one of $CH_2$ in a main chain of the alkyl group having 1 to 3 main-chain carbon atoms substituted for an oxygen atom and having two or more polymerizable functional groups, or a group derived from one of $CH_2$ in the main chain of the alkyl group having 1 to 3 main-chain carbon atoms substituted for $NR^7$ and having two or more polymerizable functional groups.

3. An electrophotographic photosensitive member according to claim 1, wherein $R^2$ represents a monovalent group represented by the following formula (2):

11. An imide compound, which is represented by the following formula (1):

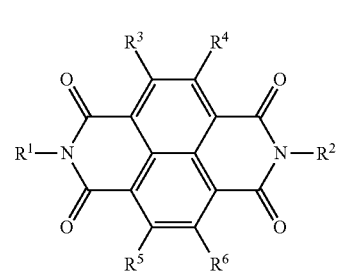

wherein, $R^1$ represents an alkyl group having 1 to 6 main-chain carbon atoms and having two or more polymerizable functional groups, a group derived from one of $CH_2$ in the main chain of the alkyl group having 1 to 6 main-chain carbon atoms substituted for an oxygen atom and having two or more polymerizable functional groups, or a group derived from one of $CH_2$ in the main chain of the alkyl group having 1 to 6 main-chain carbon atoms substituted for $NR^7$ and having two or more polymerizable functional groups;

the polymerizable functional groups is a hydroxy group, a thiol group, an amino group, or a carboxyl group;

$R^7$ represents a hydrogen atom or an alkyl group;

$R^3$ to $R^6$ each independently represent a hydrogen atom, a halogen atom, a cyano group, a nitro group, an unsubstituted or substituted alkyl group, or an unsubstituted or substituted aryl group; and $R^2$ represents a monovalent group represented by the following formula (2):

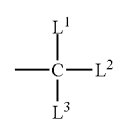

in the formula (2):

$L^1$ represents a hydrogen atom;

$L^2$ and $L^3$ each independently represent an unsubstituted or substituted alkyl group having 1 to 6 main-chain carbon atoms, a group having 1 to 6 main chain atoms and derived from one of $CH_2$ in a main chain of an unsubstituted or substituted alkyl group substituted for an oxygen atom, a group having 1 to 6 main chain atoms and derived from one of $CH_2$ in the main chain of an unsubstituted or substituted alkyl group substituted for $NR^8$, or a substituted or unsubstituted aryl group, and $R^8$ represents a hydrogen atom or an alkyl group; and a substituent of the substituted alkyl group is an alkyl group having 1 to 6 carbon atoms, a benzyl group, an alkoxycarbonyl group, or a phenyl group.

4. An electrophotographic photosensitive member according to claim 1, wherein the composition further comprises a crosslinking agent.

5. An electrophotographic photosensitive member according to claim 4, wherein the crosslinking agent is an isocyanate compound having an isocyanate group or a blocked isocyanate group, or an amine compound having an N-methylol group or an alkyl-etherified N-methylol group.

6. An electrophotographic photosensitive member according to claim 4, wherein the composition further comprises a resin having a polymerizable functional group.

7. An electrophotographic photosensitive member according to claim 6, wherein the polymerizable functional group of the resin is one of a hydroxy group, a thiol group, an amino group, a carboxyl group, and a methoxy group.

8. An electrophotographic photosensitive member according to claim 6, wherein a mass ratio between the compound represented by the formula (1), and at least one of the crosslinking agent and the resin having the polymerizable functional group in the composition is from 100:50 to 100:250.

9. A process cartridge, comprising:

the electrophotographic photosensitive member according to claim 1; and at least one unit selected from the group consisting of a charging unit, a developing unit, and a cleaning unit, the process cartridge integrally supporting the electrophotographic photosensitive member and the at least one unit, the process cartridge being removably mounted onto a main body of an electrophotographic apparatus.

10. An electrophotographic apparatus, comprising:

the electrophotographic photosensitive member according to claim 1;

a charging unit;

an exposing unit;

a developing unit; and a transferring unit.

11. An imide compound, which is represented by the following formula (1):

12. An imide compound which is represented by the following formula (1):

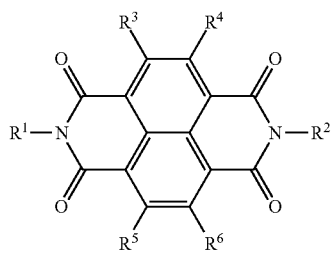

(1)

wherein
$R^1$ represents an alkyl group having 1 to 6 main-chain carbon atoms and having two or more polymerizable functional groups, a group derived from one of $CH_2$ in the main chain of the alkyl group having 1 to 6 main-chain carbon atoms substituted for an oxygen atom and having two or more polymerizable functional groups, a group derived from one of $CH_2$ in the main chain of the alkyl group having 1 to 6 main-chain carbon atoms substituted for a sulfur atom and having two or more polymerizable functional groups, or a group derived from one of $CH_2$ in the main chain of the alkyl group having 1 to 6 main-chain carbon atoms substituted for $NR^7$ and having two or more polymerizable functional groups;

the polymerizable functional groups is a hydroxy group, a thiol group, an amino group, or a carboxyl group;

$R^7$ represents a hydrogen atom or an alkyl group;

$R^3$ to $R^6$ each independently represent a hydrogen atom, a halogen atom, a cyano group, a nitro group, an unsubstituted or substituted alkyl group, or an unsubstituted or substituted aryl group; and $R^2$ represents a monovalent group represented by the following formula (3):

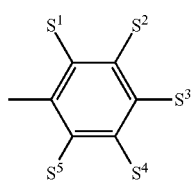

(3)

in the formula (3):
$S^1$ represents a methyl group, an ethyl group, an isopropyl group, a n-propyl group, a n-butyl group, an acyl group, an alkoxycarbonyl group, a methoxy group, an ethoxy group, a thiomethoxy group, a thioethoxy group, an aminomethoxy group, or an aminoethoxy group; and $S^2$ to $S^5$ each independently represent a hydrogen atom, a halogen atom, a cyano group, a nitro group, a methyl group, an ethyl group, an isopropyl group, a n-propyl group, a n-butyl group, an acyl group, an alkoxycarbonyl group, an alkoxy group, a thioalkoxy group, or an aminoalkoxy group.

13. An electrophotographic photosensitive member, comprising:
a support;
an undercoat layer on the support; and
a photosensitive layer on the undercoat layer, wherein the undercoat layer comprises a polymerized product of a composition comprising a compound represented by the following formula (1):

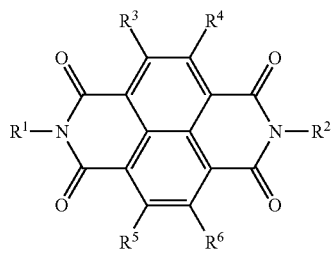

(1)

wherein,
$R^1$ represents an alkyl group having 1 to 6 main-chain carbon atoms and having two or more polymerizable functional groups, a group derived from one of $CH_2$ in the main chain of the alkyl group having 1 to 6 main-chain carbon atoms substituted for an oxygen atom and having two or more polymerizable functional groups, a group derived from one of $CH_2$ in the main chain of the alkyl group having 1 to 6 main-chain carbon atoms substituted for a sulfur atom and having two or more polymerizable functional groups, or a group derived from one of $CH_2$ in the main chain of the alkyl group having 1 to 6 main-chain carbon atoms substituted for $NR^7$ and having two or more polymerizable functional groups;

the polymerizable functional groups is a hydroxy group, a thiol group, an amino group, or a carboxyl group;

$R^7$ represents a hydrogen atom or an alkyl group;

$R^3$ to $R^6$ each independently represent a hydrogen atom, a halogen atom, a cyano group, a nitro group, an unsubstituted or substituted alkyl group, or an unsubstituted or substituted aryl group; and $R^2$ represents a monovalent group represented by the following formula (3):

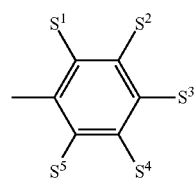

(3)

in the formula (3):
$S^1$ represents a methyl group, an ethyl group, an isopropyl group, a n-propyl group, a n-butyl group, an acyl group, an alkoxycarbonyl group, a methoxy group, an ethoxy group, a thiomethoxy group, a thioethoxy group, an aminomethoxy group, or an aminoethoxy group; and $S^2$ to $S^5$ each independently represent a hydrogen atom, a halogen atom, a cyano group, a nitro group, a methyl group, an ethyl group, an isopropyl group, a n-propyl group, a n-butyl group, an acyl group, an alkoxycarbonyl group, an alkoxy group, a thioalkoxy group, or an aminoalkoxy group.

* * * * *